United States Patent
Yanagiuchi et al.

(10) Patent No.: US 10,083,364 B2
(45) Date of Patent: Sep. 25, 2018

(54) METHOD AND APPARATUS FOR REMOVING CHARACTER BACKGROUND FROM COLORED IMAGE

(71) Applicant: GLORY LTD., Himeji-shi, Hyogo (JP)

(72) Inventors: Sayuri Yanagiuchi, Hyogo (JP); Hiroyuki Onishi, Hyogo (JP); Ryuzo Tanigawa, Hyogo (JP); Kazutaka Adachi, Hyogo (JP)

(73) Assignee: GLORY LTD., Himeji-shi, Hyogo (JP)

( * ) Notice: Subject to any disclaimer, the term of this patent is extended or adjusted under 35 U.S.C. 154(b) by 0 days.

(21) Appl. No.: 15/303,579

(22) PCT Filed: Apr. 16, 2015

(86) PCT No.: PCT/JP2015/061668
§ 371 (c)(1),
(2) Date: Oct. 12, 2016

(87) PCT Pub. No.: WO2015/159941
PCT Pub. Date: Oct. 22, 2015

(65) Prior Publication Data
US 2017/0039724 A1     Feb. 9, 2017

(30) Foreign Application Priority Data

Apr. 16, 2014  (JP) ................... 2014-085034
Apr. 16, 2014  (JP) ................... 2014-085035

(51) Int. Cl.
*G06K 9/00*     (2006.01)
*G06K 9/18*     (2006.01)
(Continued)

(52) U.S. Cl.
CPC .............. *G06K 9/18* (2013.01); *B41J 29/393* (2013.01); *B41J 29/46* (2013.01);
(Continued)

(58) Field of Classification Search
None
See application file for complete search history.

(56) References Cited

U.S. PATENT DOCUMENTS

| | | | |
|---|---|---|---|
| 5,448,651 | A | 9/1995 | Sakou et al. |
| 5,983,792 | A | 11/1999 | Yoshijima et al. |

(Continued)

FOREIGN PATENT DOCUMENTS

| | | | |
|---|---|---|---|
| JP | 2-264561 A | 10/1990 | |
| JP | 8-219999 A | 8/1996 | |

(Continued)

OTHER PUBLICATIONS

European Search Report (Application No. 15779959.4—PCT/JP2015/061668) (9 pages—dated Nov. 27, 2017.

(Continued)

*Primary Examiner* — Stephen Coleman
(74) *Attorney, Agent, or Firm* — Renner, Kenner, Greive, Bobak, Taylor & Weber

(57) ABSTRACT

Provided is a method for removing character background in a color image that obtains an image for printing evaluation by removing a background design of a character from the color image of a printed object on which the character has been printed. The method includes separating a color input image into a character part and a background part, calculating a discriminant function for separating pixels of the character part and pixels of the background part based on pixel values, and generating a background-removed image by removing the background part from the input image by using the discriminant function. Moreover, an installation adjustment method of a line camera including adjusting, based on a signal acquired by capturing an installation adjustment chart fixed to the inspection drum, an installation position of the line camera that acquires an image of a large-size printed object arranged on an inspection drum, is (Continued)

executed by using an installation adjustment chart wherein a plurality of patterns formed by white background and black vertical lines are arranged by shifting in a vertical direction so that the vertical lines continue horizontally only in a predetermined rectangular region that is elongated in a scan line direction of the line camera.

8 Claims, 24 Drawing Sheets

(51) Int. Cl.
    *B41J 29/46*     (2006.01)
    *G01N 21/892*     (2006.01)
    *G06K 9/20*     (2006.01)
    *B41J 29/393*     (2006.01)
    *G01N 21/89*     (2006.01)
    *G06T 7/00*     (2017.01)

(52) U.S. Cl.
CPC ....... *G01N 21/8901* (2013.01); *G01N 21/892* (2013.01); *G06K 9/20* (2013.01); *G06T 7/0081* (2013.01); *G01N 2201/101* (2013.01); *G06T 2207/10024* (2013.01); *G06T 2207/20144* (2013.01)

(56) References Cited

U.S. PATENT DOCUMENTS

| | | |
|---|---|---|
| 6,987,879 B1 | 1/2006 | Suino |
| 2002/0168102 A1 | 11/2002 | Lee et al. |
| 2007/0235542 A1 | 10/2007 | Tsutsumi |
| 2009/0016647 A1 | 1/2009 | Hamaguchi |
| 2013/0016154 A1 | 1/2013 | Imamura et al. |

FOREIGN PATENT DOCUMENTS

| | | | | |
|---|---|---|---|---|
| JP | 2001-174414 A | | 6/2001 | |
| JP | 2006333175 | * | 7/2006 | ............... H04N 1/41 |
| JP | 2008-269509 A | | 11/2008 | |
| JP | 2010-225013 A | | 10/2010 | |
| JP | 2014-64195 A | | 4/2014 | |

OTHER PUBLICATIONS

Yen-Lin Chen et al "Complex Document Image Segmentation using Localized Histogram Analysis with Multi-Layer Matching and Clustering" (2004 IEEE International Conference on Systems, Man and Cybematics, Piscataway, NJ, USA, vol. 4, Oct. 10, 2004 (Oct. 10, 2004), pp. 3063-3070.

Cai S et al "Recognition of Merged Characters Based on Forepart Prediction, Necessity-Sufficiency Matching, and Character-Adaptive Masing" (IEEE Transactions on Systems, Man, and Cybernetics—Part B: Cybernetics, IEEE Service Center, Piscataway, NJ, US, vol. 35, No. 1, Feb. 1, 2005 (Feb. 1, 2005), pp. 2-11.

Wang B et al "Color text image binarization based on binary texture analysis" (Pattern Recognition Letters, Elsevier, Amsterdam, NL, vol. 26, No. 10, Jul. 15, 2005 (Jul. 15, 2005), pp. 1568-1576.

Yoshida M et al "Technology for Pattern Information Processing" (Fujitsu-Scientific & Technical Journal, Fujitsu Ltd, JP, vol. 25, No. 2, Jun. 21, 1989 (Jun. 21, 1989), pp. 81-112.

\* cited by examiner

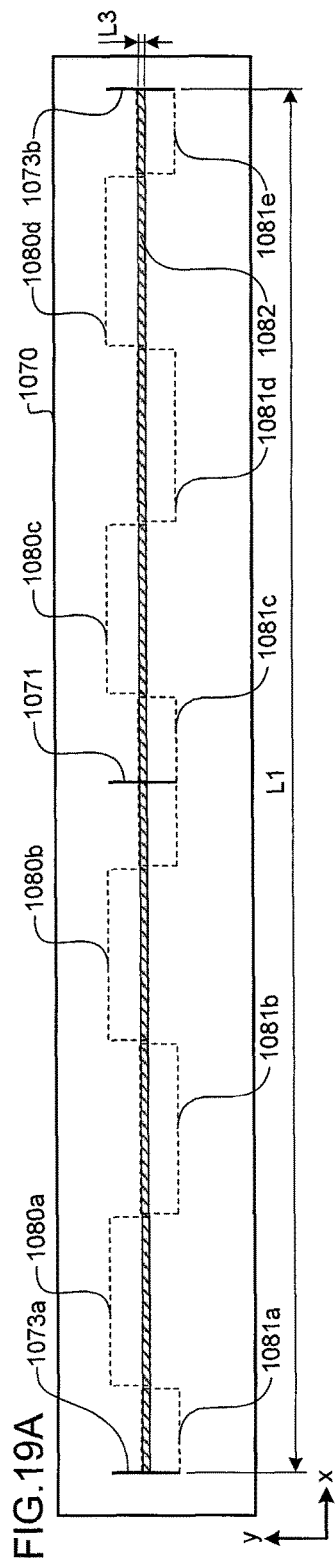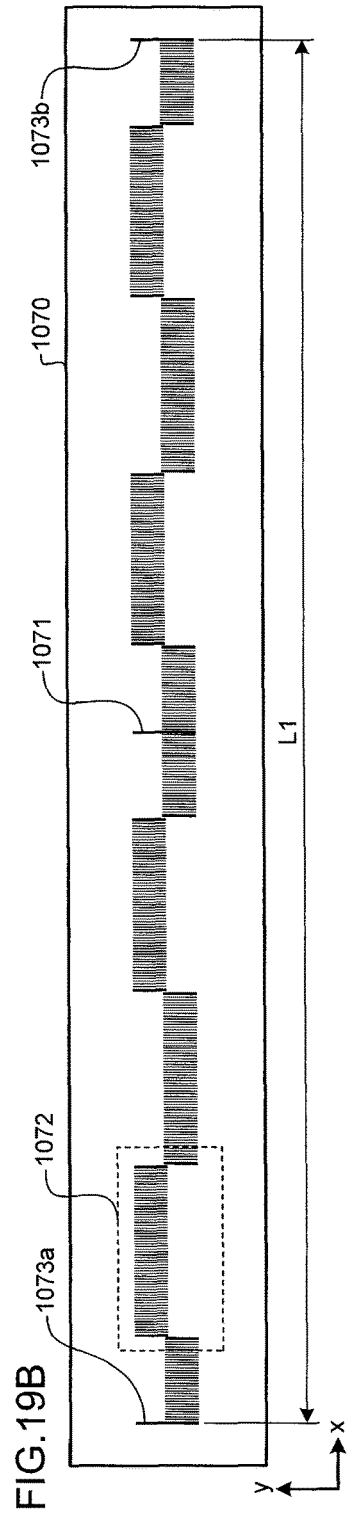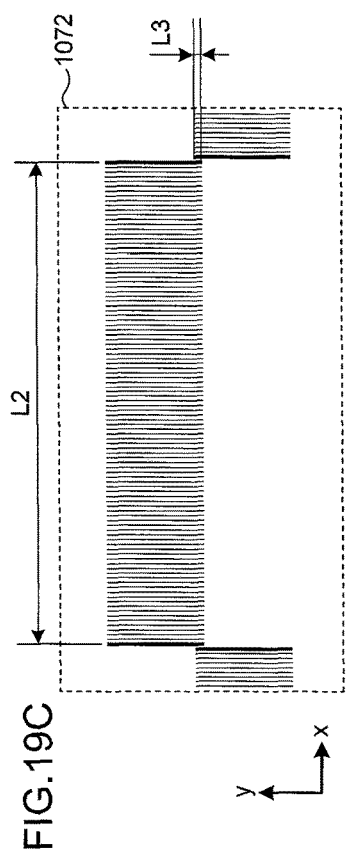

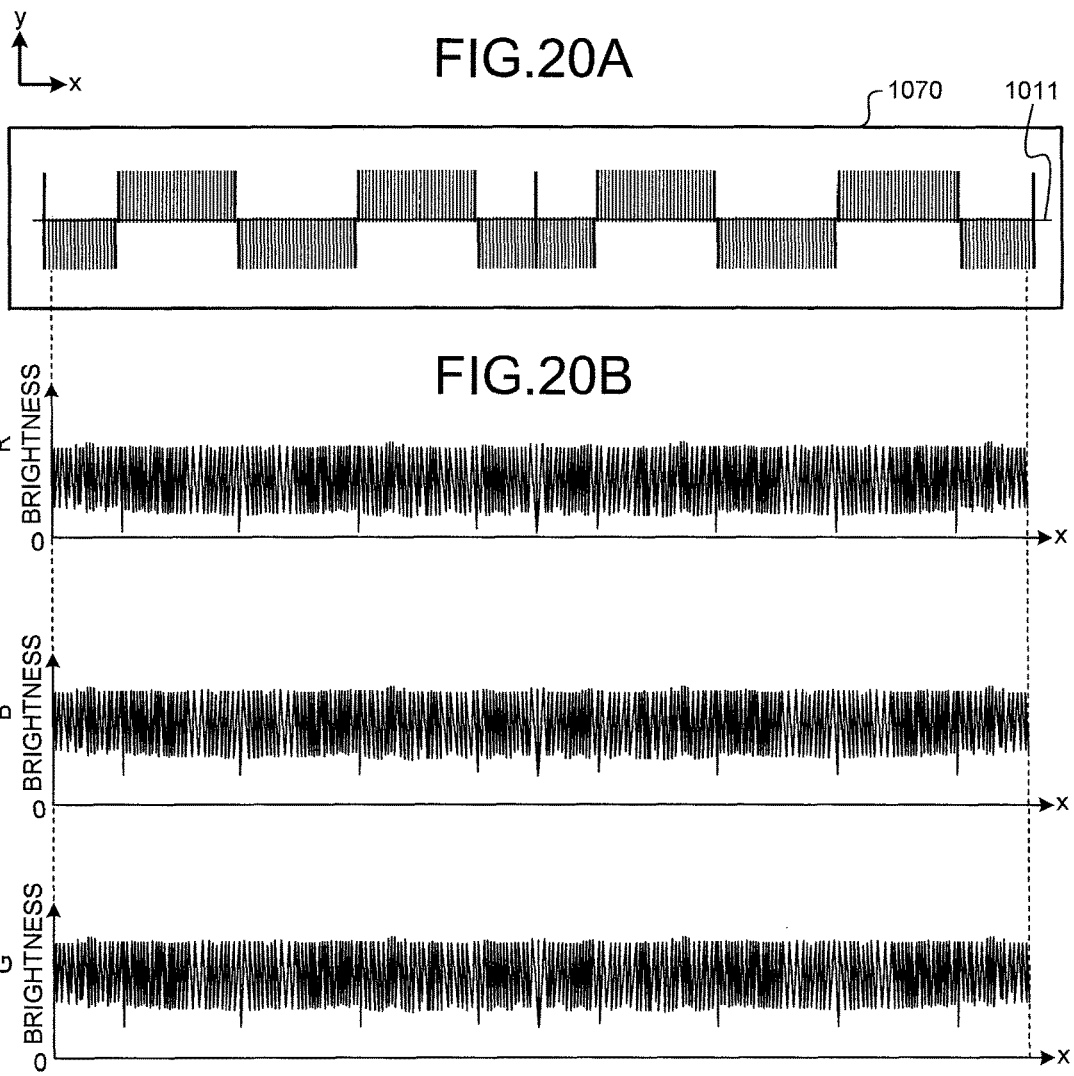

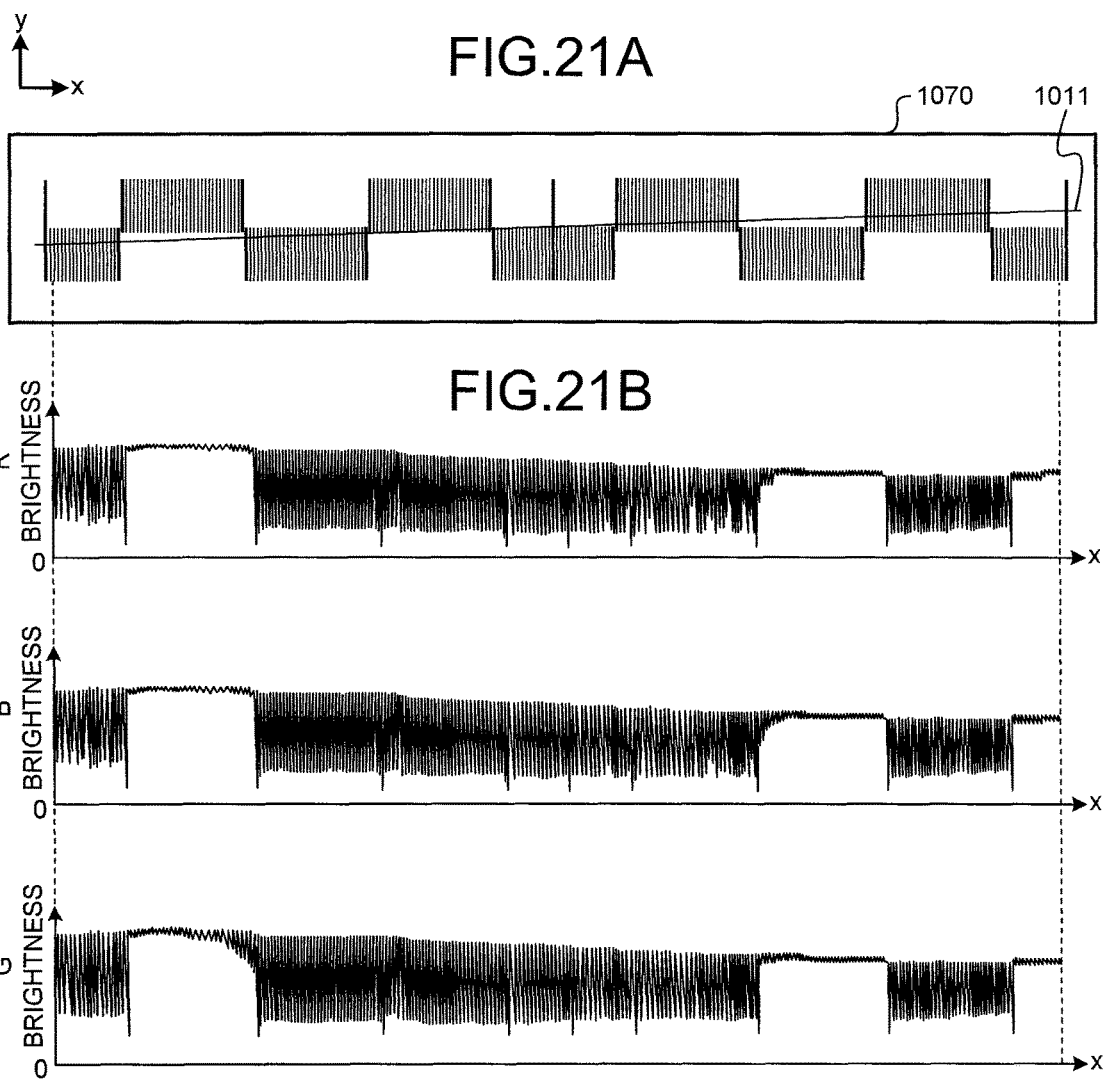

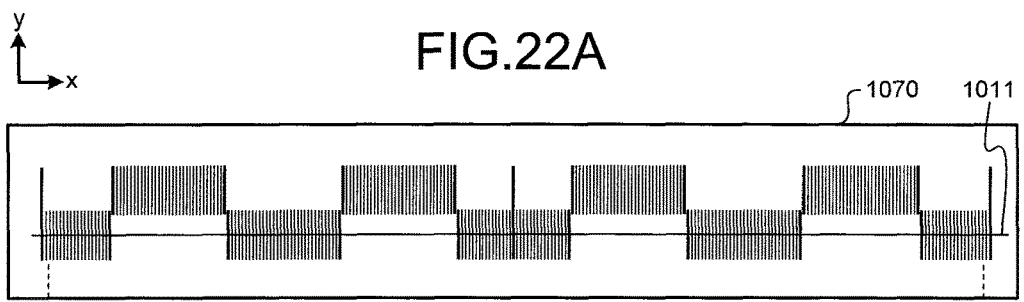
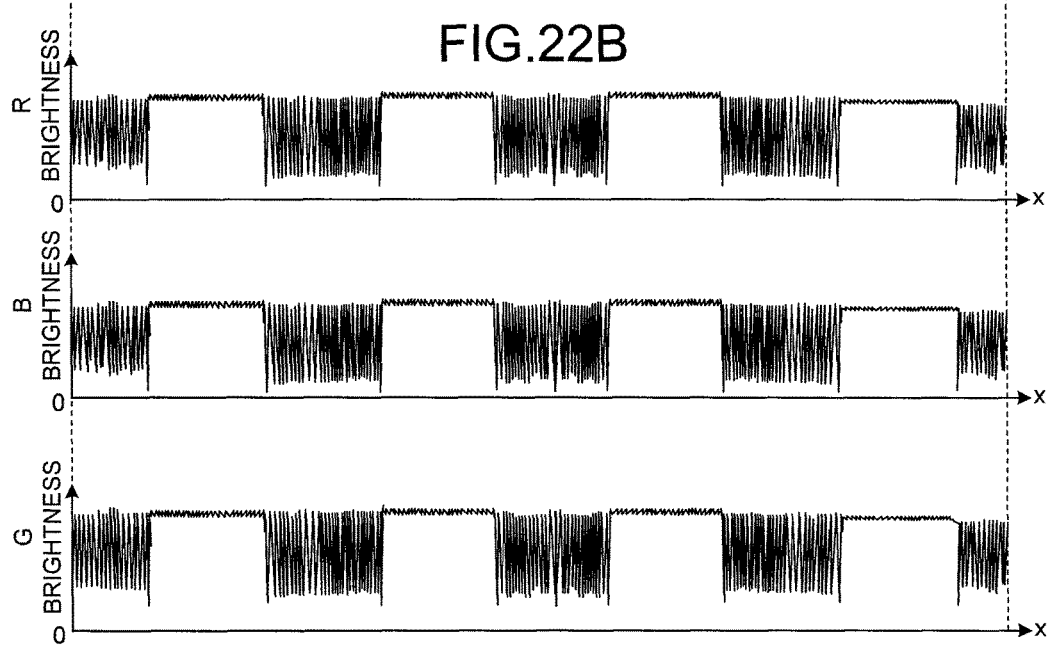

METHOD AND APPARATUS FOR REMOVING CHARACTER BACKGROUND FROM COLORED IMAGE

TECHNICAL FIELD

The present invention relates to a method and an apparatus for acquiring a character image for printing evaluation by removing a design present in the background of the character from the color image obtained by capturing a color printed object containing the character. The present invention also relates to a method and a chart for installation adjustment of a line camera that captures the large-size printed object including the above-mentioned printed object.

BACKGROUND ART

One method of printing a large number of small printed objects is to print many copies of an original one after the other. Alternatively, a large-size printed object is obtained by printing a large-size original in which the same small printed objects are arranged regularly in a matrix form, and then each of the small printed objects (hereinafter, "fragment") is cut from the large-size printed object. In the later method, printing inspection is performed to check the printing quality of each of the fragments before cutting the large-size printed object. The printing inspection is performed by using an image of the large-size printed object fixed to a large drum called an inspection drum. Such an inspection drum is included in a printing machine that prints the large-size printed object. While the inspection drum transports the large-size printed object one after the other to the following step, an image of the large-size printed object present on the inspection drum is captured with a line camera.

The printing inspection of a character contained in the color printed object is performed after removing a design present in the background of the character from the color image obtained by capturing the character. By removing the background design, the printing quality of the character can be evaluated accurately without being affected by the presence of any background design.

Various methods are available for removing the background design of the character from the color image of the printed object. For example, a color dropout processing is known in the art. In the color dropout processing, to perform character recognition processing of the characters entered in a form, lines, background patterns, and the like printed previously on the form, i.e., pixels in a color different from the color of the characters, are removed from the color image obtained by capturing the form. For example, Patent Document 1 discloses a method that allows the color dropout processing to be performed accurately. In this method, a processing object and a background pattern in a color image are separated and the background pattern is dropped out by using two gray scale values. One gray scale value is obtained based on a color of the processing object and a color of the background pattern. Another gray scale value is obtained based on a color of an area that does not contain the processing object. Moreover, another method is disclosed in Patent Document 2. In this method, pixels forming a character and pixels other than those pixels forming the character are separated based on a value obtained by performing a linear coupling of an eigenvector set previously and a brightness value of each of the pixels of a color image.

To perform the printing inspection, it is necessary to acquire an image to be used in the printing inspection with a high accuracy. To capture by a line camera a high-accuracy image of each of the large-size printed object transported one after the other on the inspection drum rotating at a high speed, it is necessary to install the line camera in a normal installation position defined with respect to the inspection drum. The installation position is defined by a position and an angle of the line camera with respect to the inspection drum.

Various methods for adjusting the installation position of a camera are known in the art. Patent Document 3 discloses a method for adjusting the installation positions of a plurality of cameras while checking an image obtained by capturing a reference pattern arranged at an imaging position. Specifically, the position of each of the cameras is adjusted so that the reference pattern contained in the image captured by each of the cameras satisfies a predetermined positional relationship. Patent Document 4 discloses a method for adjusting the installation position by capturing with a CCD sensor a line pair chart of a black-white stripe design. An installation position and the like of the CCD sensor are adjusted so that an amplitude of sine wave obtained by capturing the line pair chart becomes the maximum. Specifically, adjustment of an optical system or the adjustment of the installation position of the CCD sensor is performed based on an MTF curve so that the white and black contrast is the maximum.

CITATION LIST

Patent Document

[Patent Document 1]
  Japanese Patent Application Laid-Open No. 2002-358482
[Patent Document 2]
  Japanese Patent Application Laid-Open No. 2010-225013
[Patent Document 3]
  Japanese Patent No. 5334902
[Patent Document 4]
  Japanese Patent No. 4878570

SUMMARY OF INVENTION

Technical Problem

In the conventional methods disclosed in Patent Documents 1 and 2, sometimes the background design of the character present in the color image may not be removed. For example, when there is a light reflecting region, such as a hologram or a security thread, in the background of the character, the background may not be removed in the color dropout processing because the colors in the light reflecting region in the color image are not stable. Moreover, the printed objects come in various types such as those in which a character and a background design are printed with a similar color, in which each of the letters forming a character string is printed with a different color, in which a background design is printed with a plurality of colors. This makes it difficult to remove the background by using the conventional color dropout processing.

When processing is performed for character recognition, there is no issue as long as the character recognition result can be obtained from a remaining part of a character even if some pixels of the character are removed while removing a background of the character. However, it is preferable that the pixels that form the character are not removed when the processing is performed for the printing inspection. Moreover, if the ink to print a character scatters in the background of the character during the printing process and it causes a stain, it is required to detect the stain as a part of the printed character when evaluating the printing quality; however, this was not possible in the conventional art.

Moreover, according to the conventional art disclosed in Patent Documents 3 and 4, it is possible to adjust installation positions of cameras so that the cameras have a predetermined positional relationship, or to adjust a distance between an imaging position and an imaging device, such as a CCD, so that a focused image is obtained; however, adjustment of an inclination and the like of a line camera is difficult.

According to the method disclosed in Patent Document 3, it is possible to capture a reference pattern with two adjacent cameras and adjust a relative positional relationship between the two cameras so that the images obtained by these cameras have a predetermined positional relationship; however, it remains possible that both the cameras are installed in an inclined manner to the reference pattern. Likewise, according to the method disclosed in Patent Document 4, a focal length can be adjusted based on a stripe design stuck on an object; however, it remains possible that the camera may be inclined with respect to the object, or that the distance from the object to the camera may be different from the normal distance.

If the camera is inclined, it is possible to simply capture an image and correct the inclination of the image by performing image processing. However, the image processing takes a long time when correcting the inclination of each of the line data that is acquired line by line by scanning a large-size printed object with a line camera having several thousand pixels or more. To perform the inspection of the large-size printed object transported one after the other at a high speed by the inspection drum, it is preferable that the image data is generated from the line data output by the line camera having no inclination, but not by performing the image processing such as the inclination correction. Therefore, there is a need to realize an installation adjustment method of a line camera that will allow an installation position of the line camera to be adjusted easily while checking an installation status of the line camera, so that the installation position of the line camera matches with a normal installation position having no position misalignment or inclination with respect to an inspection drum that transports a large-size print.

The present invention was made to address the above-explained issues in the conventional art, and one object thereof is to make it possible to accurately evaluate the printing quality of a printed object. Specifically, it may be one object of the present invention to provide a method and an apparatus for acquiring a character image for printing evaluation by removing a background design of a character from the color image of a printed object on which the character has been printed. Moreover, another object of the present invention may be to provide a method and an installation adjustment chart of a line camera that allow adjustment of an installation position of the line camera while checking an installation status of the line camera, so that the line camera can be installed at a normal installation position at which a high quality image of a large-size printed object suitable for printing inspection thereof can be acquired.

Means for Solving Problems

To solve the above problem, and to achieve the above object, a method for removing a character background from a color image according to a first aspect of the present invention, which is to obtain an image for printing evaluation by removing a background design of a character from the color image of a printed object on which the character has been printed, includes, separating a color input image into a character part and a background part; calculating a discriminant function for separating pixels of the character part and pixels of the background part based on pixel values; and generating the background-removed image by removing the background part from the input image by using the discriminant function.

In the above method for removing a character background in a color image, the separating includes identifying a position at which a font image of the character contained in the input image overlaps with the character contained in the input image, and determining, among pixels that form the input image, pixels at a position overlapping the font image as the character part, and pixels at a position not overlapping the font image as the background part.

In the above method for removing a character background in a color image, the calculating includes calculating the discriminant function by performing linear distinction processing.

The above method for removing a character background in a color image, further includes specifying a character range for calculating the discriminant function, wherein the separating includes separating the input image into the character part and the background part based on the character range specified at the specifying, and the calculating includes calculating the discriminant function based on the character range specified at the specifying.

In the above method for removing a character background in a color image, the method is performed for every character when a plurality of characters is contained in the input image.

The above method for removing a character background in a color image further includes performing binarization of the background-removed image to remove the background design having a similar color as that of the character.

The above method for removing character background in a color image further includes acquiring the input image from the color image captured from a large-size printed object.

A character background removing apparatus according to a second aspect of the present invention, that obtains an image for printing evaluation by removing a background design of a character from the color image of a printed object on which the character has been printed, includes a character-background removing unit that separates a color input image into a character part and a background part, calculates a discriminant function for separating pixels of the character part and pixels of the background part based on pixel values, and generates a background-removed image by removing the background part from the input image by using the discriminant function.

The above character background removing apparatus further includes an operation unit that specifies a position of the character on the input image. The character-background removing unit separates the input image into the character part and the background part based on the position of the character specified by the operation unit. The character-background removing unit calculates the discriminant function for separating the pixels of the character part and the pixels of the background part based on pixel values and generates the background-removed image by removing a background design by using the discriminant function.

Moreover, to solve the above problem, and to achieve the above object, an installation adjustment method of a line camera according to a third aspect of the present invention, which includes adjusting, based on a signal acquired by capturing an installation adjustment chart fixed to the inspection drum, an installation position of the line camera that captures an image of a large-size printed object arranged on an inspection drum, includes capturing with the line camera the installation adjustment chart on which a plurality of patterns formed by white background and black vertical lines are arranged by shifting in a vertical direction so that the vertical lines continue horizontally only in a predetermined rectangular region that is elongated in a scan line direction of the line camera; and displaying on a display unit an imaging signal indicating a signal waveform that varies according to an installation status of the line camera and that is obtained by the line camera by capturing the installation adjustment chart.

The above installation adjustment method of a line camera further includes, judging in which a camera-position judging unit judges the installation status of the line camera based on the signal waveform of the imaging signal obtained by the line camera; and informing in which the camera-position judging unit informs a judgment result obtained at the judging.

In the above installation adjustment method of a line camera, an overlapping width of the patterns along a scan line when the line camera is installed at a normal installation position is equal to a width in the vertical direction of the predetermined rectangular region, and the width is set based on an allowable error in the installation position of the line camera.

In the above installation adjustment method of a line camera, each of the patterns included in the installation adjustment chart is formed of a plurality of vertical lines arranged horizontally at a predetermined interval, and the vertical lines in the predetermined rectangular region are formed by at least a part of the vertical lines.

In the above installation adjustment method of a line camera, a thickness of some vertical lines is different from a thickness of the other vertical lines in the predetermined rectangular region.

In the above installation adjustment method of a line camera, each of the patterns included in the installation adjustment chart has a rectangle shape formed by vertical lines having a predetermined length.

In the above installation adjustment method of a line camera, each of the patterns included in the installation adjustment chart is arranged by shifting alternately in the vertical direction.

In the above installation adjustment method of a line camera, the white background and the black vertical lines that form the installation adjustment chart are arranged so as to have a one-to-one correspondence with pixels of the line camera.

The above installation adjustment method of a line camera further includes adjusting the installation position of the line camera so that the signal waveform of the imaging signal obtained by the line camera and displayed on the display unit matches with a reference signal waveform obtained when the installation adjustment chart is captured with the line camera installed at the normal installation position.

In the above installation adjustment method of a line camera, the adjusting includes correcting, when the signal waveform of the imaging signal obtained by the line camera indicates that a part of the patterns on the right of a center of the installation adjustment chart and a part of the patterns on the left of the center are not captured, an inclination of the line camera by rotating the line camera about an optic axis thereof.

In the above installation adjustment method of a line camera, the adjusting includes correcting, when the signal waveform of the imaging signal obtained by the line camera indicates that only the patterns that are shifted vertically above or only the patterns that are shifted vertically below on the installation adjustment chart are captured, the inclination of the line camera by rotating the line camera about a horizontal axis that is orthogonal to the optic axis thereof.

In the above installation adjustment method of a line camera, the adjusting includes correcting, when the signal waveform of the imaging signal obtained by the line camera has a waveform that will be obtained by shifting in a left direction or a right direction the reference signal waveform obtained when the installation adjustment chart is captured with the line camera installed at the normal installation position, the inclination of the line camera by rotating the line camera about a vertical axis thereof.

In the above installation adjustment method of a line camera, the adjusting includes adjusting, when a length in an horizontal direction of the installation adjustment chart indicated by the signal waveform of the imaging signal obtained by the line camera is different from a length in the horizontal direction of the installation adjustment chart indicated by the reference signal waveform obtained when the installation adjustment chart is captured with the line camera installed at the normal installation position, a distance between the line camera and the inspection drum by moving the line camera in a front-back direction.

A chart for installation adjustment of a line camera according to a fourth aspect of the present invention, which is fixed to an inspection drum for adjusting an installation position of the line camera that acquires an image of a large-size printed object fixed to the inspection drum, based on a signal acquired by capturing with the line camera, includes a predetermined rectangular region that is elongated in a scan line direction of the line camera in which white background and black vertical lines are arranged so that the vertical lines continue horizontally only therein.

In the above chart for installation adjustment of a line camera, the predetermined rectangular region is formed by a plurality of patterns formed by arranging the white background and the black vertical lines by shifting in a vertical direction.

Advantageous Effects of Invention

According to the present invention, a color input image is separated into a character part and a background part based on a result of character recognition of the color image that contains a character, and a discriminant function for separating the character part and the background part based on pixel values is calculated and thereafter the background part is removed from the input image by using the discriminant function. Therefore, in cases such as when there is a stain of the ink used for printing the character or when a portion of the printed character is missing and the background can be seen through the missing portion, such stain or missing portion can be detected. As a result, printing evaluation of the character can be performed.

Moreover, according to the present invention, the character part and the background part are separated after identifying a position of the character in the input image based on a font image of the character contained in the input image. Therefore, the character part and the background part can be separated accurately.

Moreover, according to the present invention, the process for removing the background design from the color image including the character is performed per character. Accordingly, the background part of each of the characters can be removed even in cases such as when each of the characters is printed with a different color, each of the characters is printed in a different font, and a color and a design of the background of each of the characters are different.

Moreover, according to the present invention, noise is removed by performing binarization processing based on pixel values of pixels that form the character. As a result, an image of only the character can be obtained even if noise is present due to a design of similar color as the character in the image obtained by removing the background design from the input image by using the discriminant function.

Moreover, according to the present invention, in an installation adjustment chart, a plurality of patterns formed by white background and black vertical lines are arranged by shifting in a vertical direction so that the vertical lines continue horizontally only in a predetermined rectangular region that is elongated in a scan line direction of a line camera. As a result, an installation position of the line camera can be adjusted to a normal installation position by checking a signal waveform obtained by capturing the installation adjustment chart with the line camera so that a reference signal waveform that would be obtained by capturing the vertical lines in this rectangular region is obtained.

Moreover, according to the present invention, an installation status of the line camera is determined and informed by a camera-position judging unit. As a result, the installation position of the line camera can be adjusted based on this information.

Moreover, according to the present invention, a width in the vertical direction of the predetermined rectangular region in which the vertical lines continue horizontally is set based on an allowable error in the installation position of the line camera. As a result, by adjusting the installation position of the line camera so that a reference signal waveform that would be obtained by capturing the vertical lines in this rectangular region is obtained, the line camera can be installed at the normal installation position within an allowable error.

Moreover, according to the present invention, each of the patterns included in the installation adjustment chart is formed so that a different signal waveform is obtained depending on an inclination or the installation position of the line camera. As a result, whether the adjustment of the installation position of the line camera is necessary can be recognized from the obtained signal waveform.

Moreover, according to the present invention, the white background and the black vertical lines that form the installation adjustment chart are arranged so as to have a one-to-one correspondence with pixels of the line camera. As a result, an abnormality of a light receiving element of the line camera can be determined on a pixel-by-pixel basis.

Moreover, according to the present invention, each of the patterns in the installation adjustment chart is arranged by shifting in the vertical direction, or thicknesses of the vertical lines is set different to allow recognition of a center or a border of each of the patterns. As a result, a direction in which the inclination or the position misalignment of the line camera needs to be corrected can be recognized from the signal waveform obtained by the line camera.

BRIEF DESCRIPTION OF DRAWINGS

FIGS. 19A to 19C are views indicating an installation adjustment chart.

FIGS. 20A and 20B are views indicating a relation between the installation adjustment chart and a reference signal waveform acquired when a line camera is installed at a normal installation position.

FIGS. 21A and 21B are views indicating a relation between the installation adjustment chart and a signal waveform obtained when the line camera is inclined.

FIGS. 22A and 22B are other examples of views indicating the relation between the installation adjustment chart and the signal waveform obtained when the line camera is inclined.

DESCRIPTION OF EMBODIMENTS

Exemplary embodiments of a method and an apparatus for removing character background from a color image, and a method and an installation adjustment chart of a line camera according to the present invention are explained below with reference to the accompanying drawing.

First Embodiment

At first, a method and an apparatus for removing character background from a color image is explained. The method for removing character background according to the present embodiment is implemented, for example, on a color image of a large-size printed object captured by a line camera. As one process of printing inspection of each of the fragments of the large-size printed object, a printing quality of a character printed on each of the fragments is evaluated. To accurately evaluate the printing quality of the character, first, a character image is acquired by removing a background design of the character by using the method for removing character background according to the present embodiment, and then, the printing inspection of this character image is performed.

Figure 1:
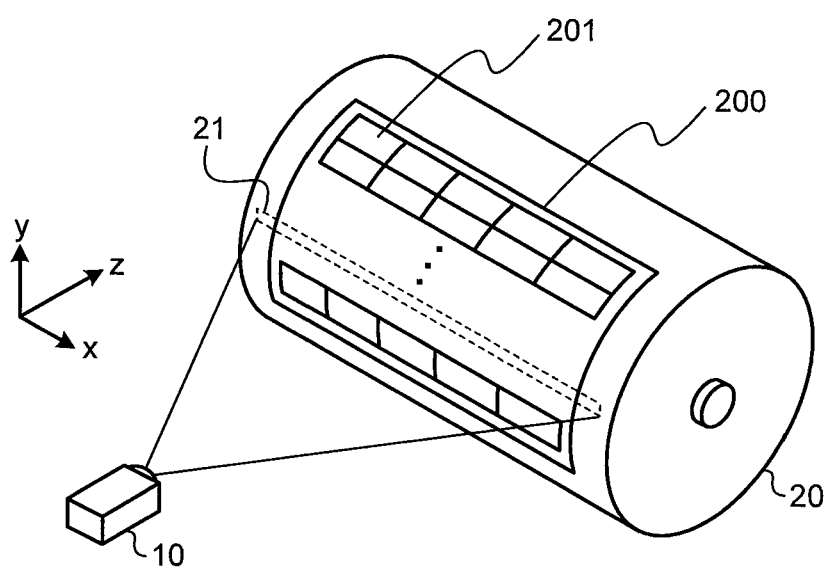
FIG. 1 is a schematic diagram for explaining a method of acquiring a color image of a large-size printed object.

FIG. 1 is a schematic diagram for explaining a method for acquiring a color image of a large-size printed object 200. In a large-scale printing machine, a color image of the large-size printed object 200 containing a plurality of fragments 201 is acquired by a line camera 10 while the large-size printed object 200 is being rotated and transported by an inspection drum 20. In FIG. 1, the x-axis direction corresponds to the horizontal direction and the y-axis direction corresponds to the vertical direction. The line camera 10 is installed so that an optic axis direction thereof corresponds to the z-axis direction. The inspection drum 20 is rotatably supported by a rotation axis that is parallel to the x-axis. The inspection drum 20 is rotationally driven by a not-shown inspection-drum driving unit. When the inspection drum 20 rotates, the large-size printed object 200 fixed to an outer peripheral surface of the inspection drum 20 passes an imaging region 21 (the region shown with a dashed line in the drawing) of the line camera 10 at a speed of 4 m/s, for example.

The line camera 10 includes an imaging device in which a plurality of light receiving elements of each of the RGB colors is arranged in one direction. The line camera 10 acquires R (red) line data, G (green) line data, and B (blue) line data by capturing the large-size printed object line by line, and generates an R image, a G image, and a B image from the acquired line data. Moreover, the line camera 10 generates a full color image by using these images. The imaging device of the line camera 10 has, for example, 8192 pixels in one line.

Figure 2:
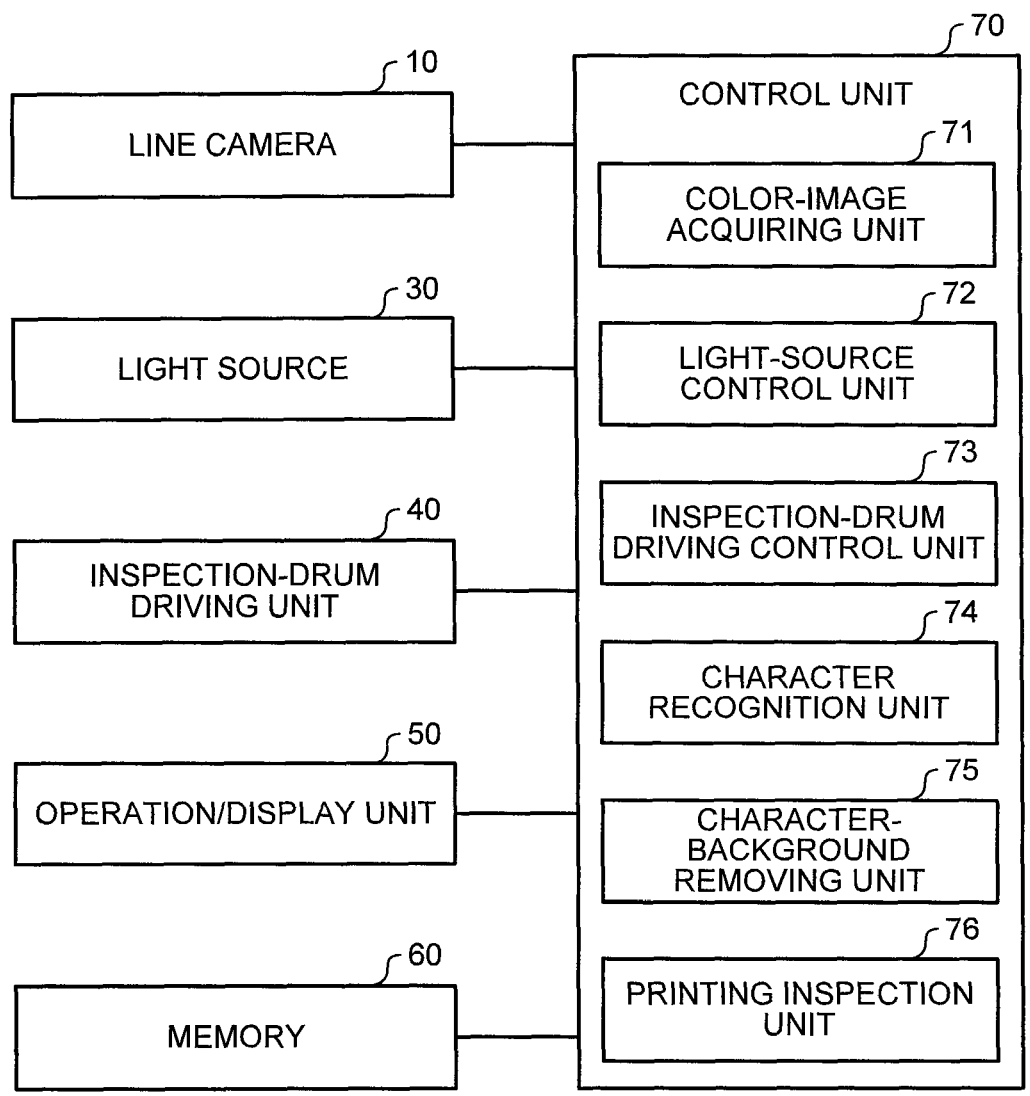
FIG. 2 is a block diagram of a general configuration of a character background removing apparatus according to a first embodiment.

Subsequently, a configuration of the character background removing apparatus is explained. FIG. 2 is a block diagram of a general configuration of the character background removing apparatus. The character background removing apparatus includes, besides the line camera 10 shown in FIG. 1, a light source 30, an inspection-drum driving unit 40, an operation/display unit 50, a memory 60, and a control unit 70.

The light source 30 illuminates the imaging region 21 of the line camera 10 on the inspection drum 20. If a partial region that reflects the irradiated light, such as a hologram or a security thread, is present in the fragment 201 of the large-size printed object, and the light reflected from such a partial region directly enters the line camera 10, a brightness difference between this partial region and the other region in the fragment 201 becomes large. It causes so-called blown out highlights or blocked up shadows. To address this issue, the light source 30 is installed by adjusting a position thereof so that the light reflected from the large-size printed object 200 does not directly enter the line camera 10.

The inspection-drum driving unit 40 rotationally drives the inspection drum 20 by using a motor and the like. The inspection-drum driving unit 40 detects a rotation angle and a rotation position of the inspection drum 20 by using a rotary encoder and the like.

The operation/display unit 50 includes a touch panel-type liquid crystal display device and the like. The operation/display unit 50 displays various pieces of information and receives input of various pieces of information. The operation/display unit 50 displays, for example, an image captured with the line camera 10, and setting information relating to background removal processing. Moreover, the operation/display unit 50 receives input of, for example, setting operation relating to the background removal processing.

The memory 60 is a nonvolatile storage device such as a hard disk and a semiconductor memory. The memory 60 is used to store therein various pieces of data required in the background removal processing. The memory 60 is used to store, for example, an image that is a processing object in the background removal processing, and setting information relating to the background removal processing. The memory 60 stores therein dictionary data required in character recognition processing. The control unit 70 includes a color-image acquiring unit 71, a light-source control unit 72, an inspection-drum driving control unit 73, a character recognition unit 74, a character-background removing unit 75, and a printing inspection unit 76.

Figure 3A:
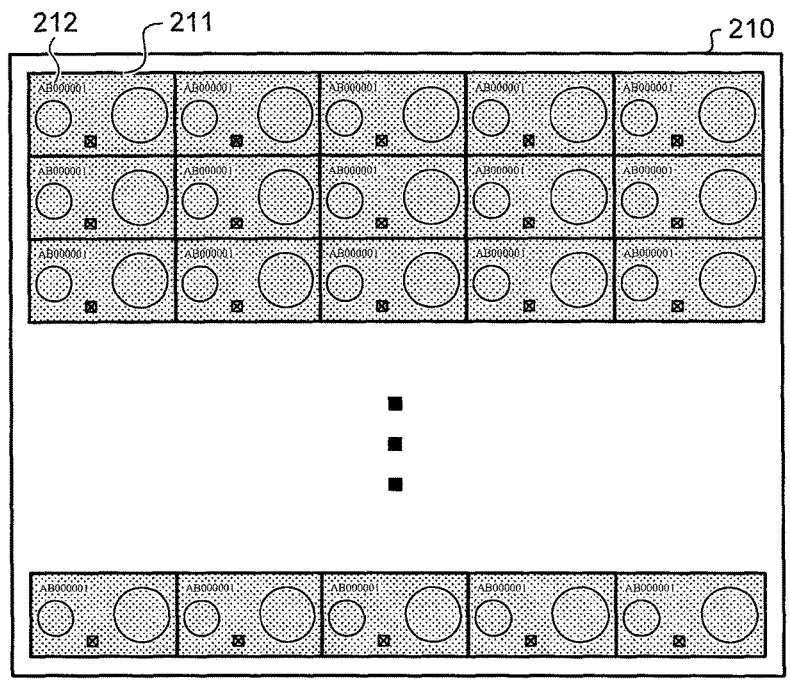
FIGS. 3A to 3C are schematic diagrams of an exemplary color image acquired from a large-size printed object.
Figure 3B:
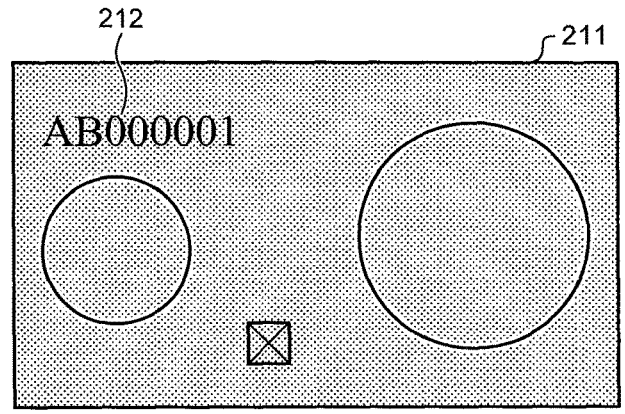
Figure 3C:
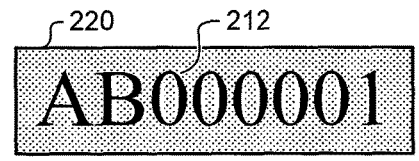

The color-image acquiring unit 71 captures the large-size printed object 200 by using the line camera 10 to acquire the color image of the large-size printed object 200. Moreover, the color-image acquiring unit 71 cuts out a partial region image from the acquired color image. This partial region image is used as a processing object in a character-background removal processing. FIGS. 3A to 3C are schematic diagrams of an exemplary color image acquired from the large-size printed object 200 by the color-image acquiring unit 71. Although FIGS. 3A to 3C are schematic representations, an image 210 of the large-size printed object 200, an image 211 of the fragment 201, and an image 220 containing a character string are all color images.

Specifically, the color-image acquiring unit 71 acquires the color image 210 of the entire large-size printed object 200 as shown in FIG. 3A. The color image 210 is obtained from the line data obtained by scanning with the line camera 10 line by line the transported large-size printed object 200 that is being rotated by the inspection drum 20. The line camera 10 acquires the line data while the light-source control unit 72 performs control to illuminate the surface of the large-size printed object 200.

For example, the color image 210 of the large-size printed object includes a plurality of the fragment images 211 each having a background design on the entire thereof. As shown in FIG. 3B, each of the fragment images 211 contains a character string 212 that represents an identification number used for identifying each fragment. After printing the large-size printed object 200, evaluation of the printing quality of the character string 212 printed in the fragment 201 is performed. For this purpose, as shown in FIG. 3C, the color-image acquiring unit 71 cuts out from the color image 210 shown in FIG. 3A the color image 220 of the partial region containing the character string 212. Specifically, based on the information set previously regarding the large-size printed object 200, the color-image acquiring unit 71 recognizes a position and a size of the character string 212 in each of the fragment 201 contained in the color image 210 of the large-size printed object 200. Then, the color-image acquiring unit 71 cuts out the color image 220 of the partial region containing the character string 212. The color-image acquiring unit 71 stores in the memory 60 the cut color image 220 as an input image. This input image is later input into the character recognition unit 74 and the character-background removing unit 75.

The light-source control unit 72 adjusts an illuminance of the light output from the light source 30 depending on a temperature variation and a degradation state of the light source 30. The inspection-drum driving control unit 73 controls the inspection-drum driving unit 40 to control the rotation of the inspection drum 20. The inspection-drum driving control unit 73 recognizes the rotation position of the inspection drum 20. While the white light is being output from the light source 30 under the control of the light-source control unit 72, the color-image acquiring unit 71 controls an imaging timing of the line camera 10 depending on the rotation position of the inspection drum 20 recognized by the inspection-drum driving control unit 73 and acquires the line data by scanning the large-size printed object 200 on the inspection drum 20 line by line.

The character recognition unit 74 performs character recognition of the character string contained in the input image acquired by the color-image acquiring unit 71. The character-background removing unit 75 generates the background-removed image by removing from the input image the design present in the background of the character. The printing inspection unit 76 evaluates the printing quality of the character based on the image that contains only the character after the background design has been removed therefrom.

Subsequently, the character recognition processing, the background removal processing and the printing evaluation processing will be explained. In the following, to simplify the explanation, each of the processing will be explained by using, as an input image 301, a color image that contains only one character. When the input image contains a character string including a plurality of characters, the processing explained below shall be executed for each of the characters constituting the character string.

Figure 4:
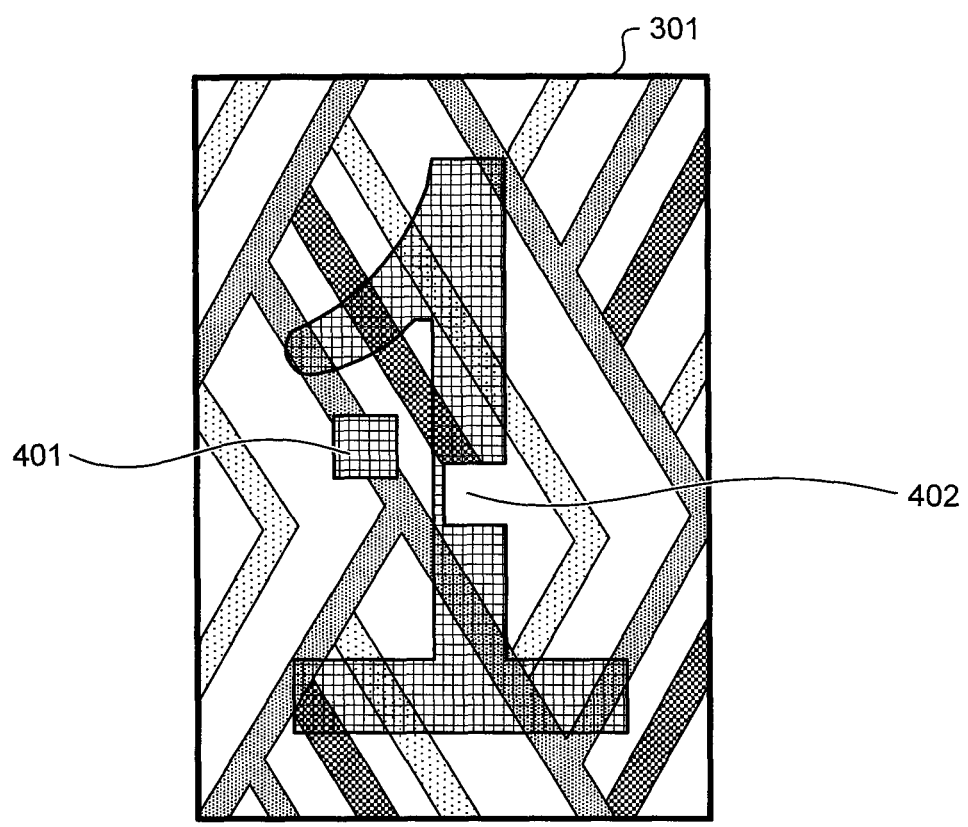
FIG. 4 is a schematic diagram of an exemplary input image obtained by cutting the color image of the large-size printed object.

FIG. 4 is a schematic diagram of the exemplary input image 301 obtained by the color-image acquiring unit 71 by cutting out the color image of the large-size printed object 200. Although FIG. 4 is a schematic representation, the input image 301 is a color image obtained by capturing a character (number "1") with red ink printed on a background design. The background design is a line design containing many blue straight lines, green straight lines, and red straight lines on a white background. This input image 301 is an example of an image having unsatisfactory printing quality as it contains a stain 401 and a missing portion 402. The stain 401 is ink used for printing the character but stuck to a region other than the character. The missing portion 402 is a part of the character missing due to absence of the ink and from where the background design is exposed.

Figure 5:
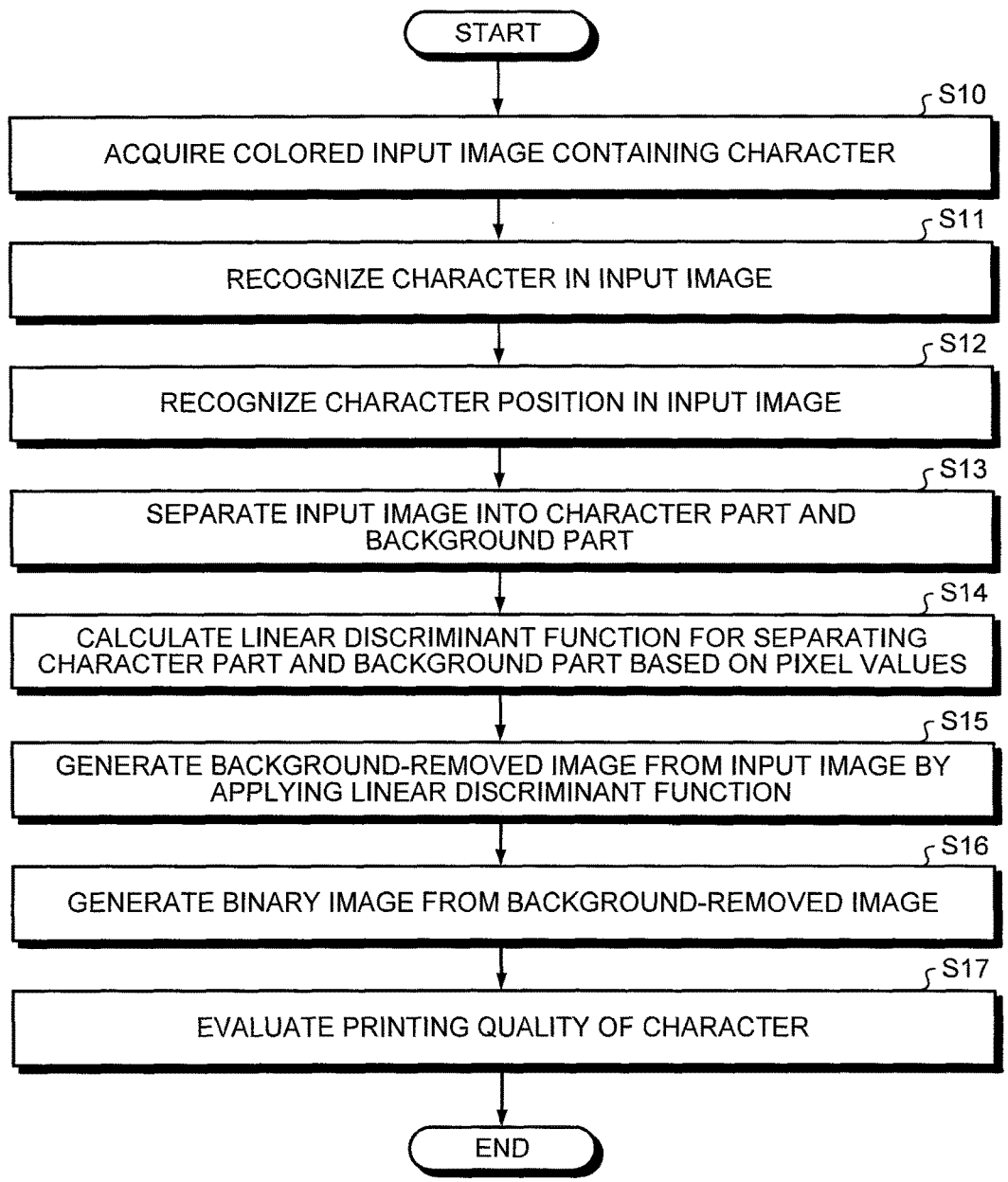
FIG. 5 is a flowchart indicating a flow of processing from acquisition of the input image up to performing a printing evaluation of a character.

FIG. 5 is a flowchart indicating a flow of the processing from acquisition of the input image 301 up to performing the printing evaluation of the character. When the input image 301 shown in FIG. 4 is acquired by the color-image acquiring unit 71 (Step S10), the character recognition unit 74 performs the character recognition processing of the input image 301 (Step S11). Character font images of all the characters that may be recognized in the character recognition processing are previously registered in the dictionary data stored in the memory 60. For example, the character recognition unit 74 recognizes the character by identifying the character contained in the input image 301 by performing an image matching processing between the input image 301 and the character font images of the characters registered in the dictionary data. Image magnification is previously adjusted so that the size of the character contained in the input image 301 matches with that of the character contained in the character font images.

Figure 6:
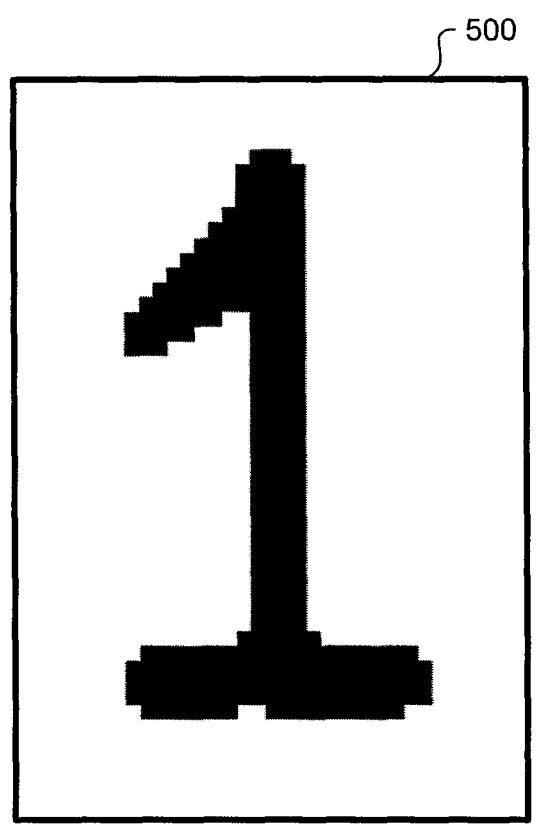
FIG. 6 is a view of an exemplary font image registered in dictionary data.

FIG. 6 depicts a font image 500 of the character "1" registered in the dictionary data. As a result of the image matching processing with the input image 301 shown in FIG. 4 and the font image 500 shown in FIG. 6, when a character recognition result that the character "1" is contained in the input image 301 is obtained by the character recognition unit 74, the character-background removing unit 75 recognizes a character position in the input image 301 (Step S12). Specifically, the position of the font image 500 on the input image 301 at a timing when it is determined in the image matching processing that the character contained in the input image 301 matches with the font image 500 is recognized as the character position in the input image 301.

Subsequently, based on the recognized character position in the input image 301, the character-background removing unit 75 separates the input image 301 into a character part and a background part (Step S13). For this purpose, specifically, the font image 500 shown in FIG. 6 is overlapped on the character position of the input image 301. In this state, among the pixels that constitute the input image 301 shown in FIG. 4, the pixels present at the position overlapping with the pixels that constitute the font image 500 are considered to constitute the character part, and the pixels present at the position that does not overlap with the pixels that constitute the font image 500 are considered to constitute the background part.

Figure 7A:
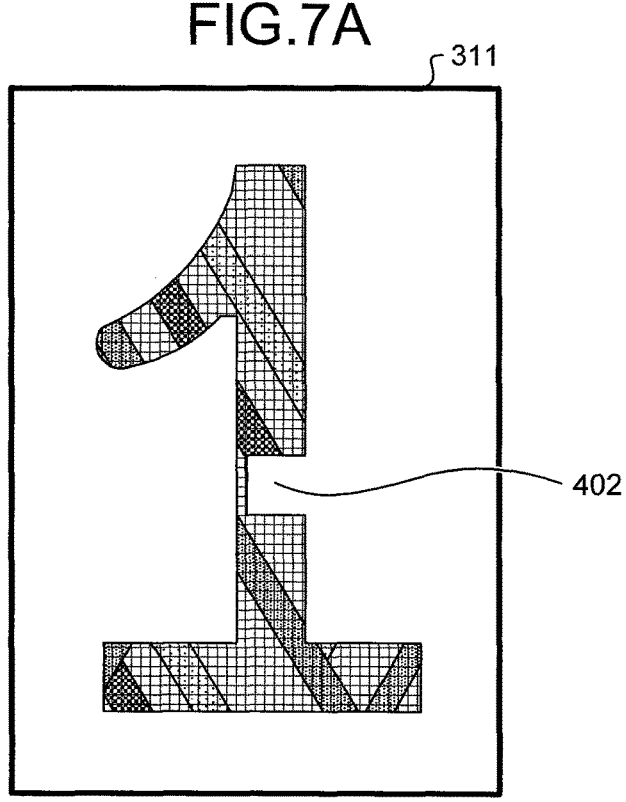
FIGS. 7A and 7B are schematic diagrams indicating an image of a character part and an image of a background part both of which are separated from the input image.
Figure 7B:
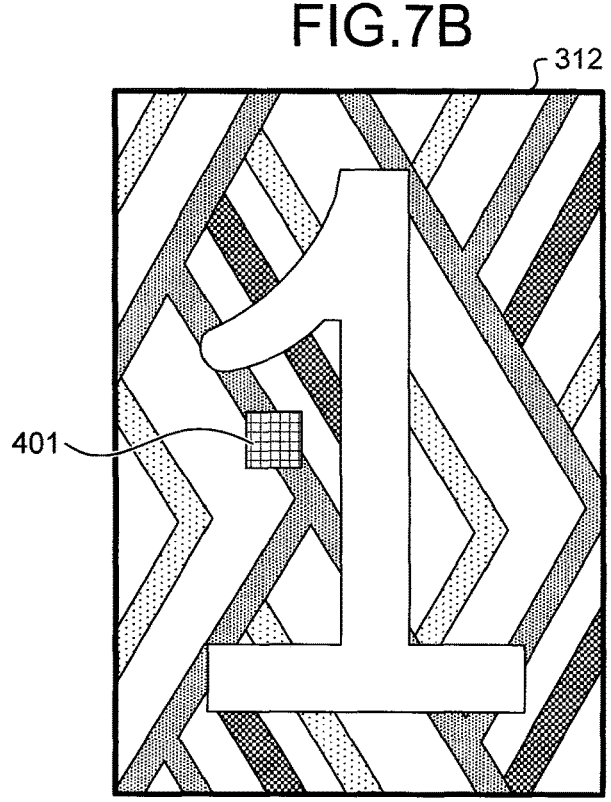

FIG. 7A is a schematic diagram of a character part image 311 constituted by the pixels of the character part obtained from the input image 301 shown in FIG. 4. FIG. 7B is a schematic diagram of a background part image 312 constituted by the pixels of the background part obtained from the input image 301 shown in FIG. 4. Although FIGS. 7A and 7B are schematic representations, the character part image 311 in FIG. 7A is a color image of the character printed with red ink, and the background part image 312 in FIG. 7B is a color image of the background design containing the blue straight lines, green straight lines, and red straight lines on the white background.

As shown in FIGS. 7A and 7B, when the character part and the background part are separated based on the position and the shape of the character by using the font image 500, the background part image 312 contains the stain 401 at the position that does not overlap with the font image 500. That is, because the stain 401 is regarded as the background, the printing inspection cannot be performed appropriately.

In this manner, after separating the input image 301 into the character part image 311 and the background part image 312, the character-background removing unit 75 calculates a discriminant function based on pixel values of all the R, G, B pixels that constitute the character part image 311 and pixel values of all the R, G, B pixels that constitute the background part image 312 (Step S14). This discriminant function is used in separating the pixels of the character part and the pixels of the background part based on the respective pixel values. A linear discriminant function or a nonlinear discriminant function can be used as the discriminant function, for example. In the following explanation, the linear discriminant function is used as the discriminant function as an example. Specifically, the pixel values of each of the R, G, B pixels constituting the input image 301 are converted by using a linear discriminant function $V=W1\times R+W2\times G+W3\times B+W4$. Weights W1 to W4 in this linear discriminant function are calculated so that an image from which the background of the character has been removed is obtained. Because this processing can be performed by using a conventional linear distinction processing (LDA: Linear Discriminant Analysis), the detailed explanation thereof has been omitted.

Figure 8A:
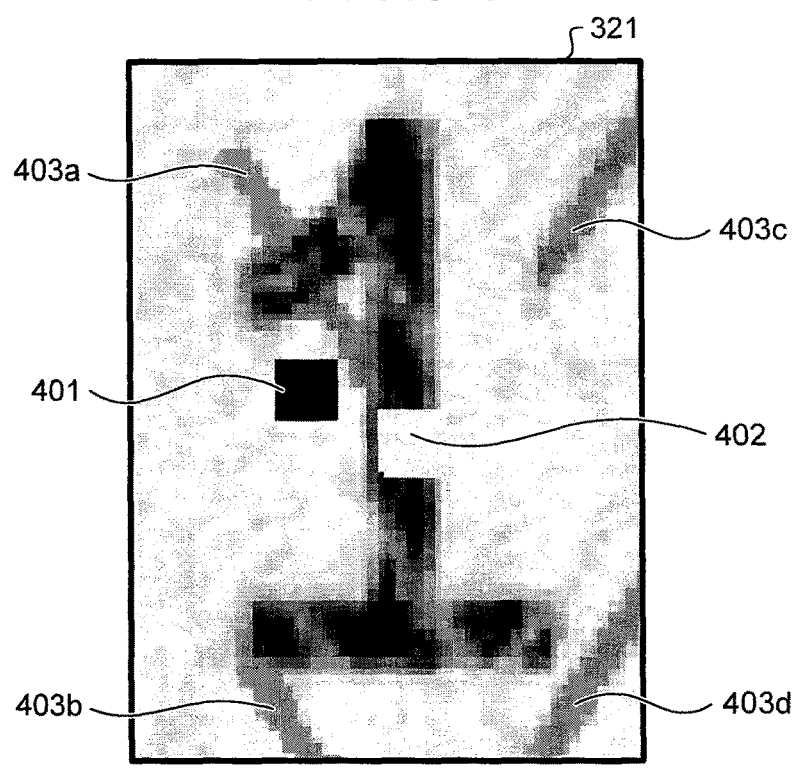
FIGS. 8A and 8B are views of a background-removed image generated from the input image by using a discriminant function and a character image generated from the background-removed image with a binarization processing.

After obtaining the linear discriminant function, the character-background removing unit 75 applies this function to the pixel values of each of the pixels constituting the input image 301 shown in FIG. 4 thereby generating the background-removed image (Step S15). The background-removed image is an image from which almost all the pixels constituting the background part have been removed from the input image 301. FIG. 8A shows a background-removed image 321 generated from the input image 301 shown in FIG. 4. The background-removed image 321 is a gray image obtained by converting the pixel values of the R, G, B pixels by using the linear discriminant function. In this manner, by removing the background by using the linear discriminant function, the stain 401 is left behind, without being removed from the background-removed image 321, as a part of the ink constituting the character.

As shown in FIG. 8A, in the background-removed image 321, among the background design contained in the input image 301, some of the pixels having a similar color as that of the character "1" may be left behind as noise 403a to 403d. However, the pixels constituting the noise have different pixel values than the pixels constituting the character in the background-removed image 321. Accordingly, the noise 403a to 403d can be removed by executing binarization processing by using a threshold value that is determined so that the pixels constituting the character are to be left behind.

Figure 8B:
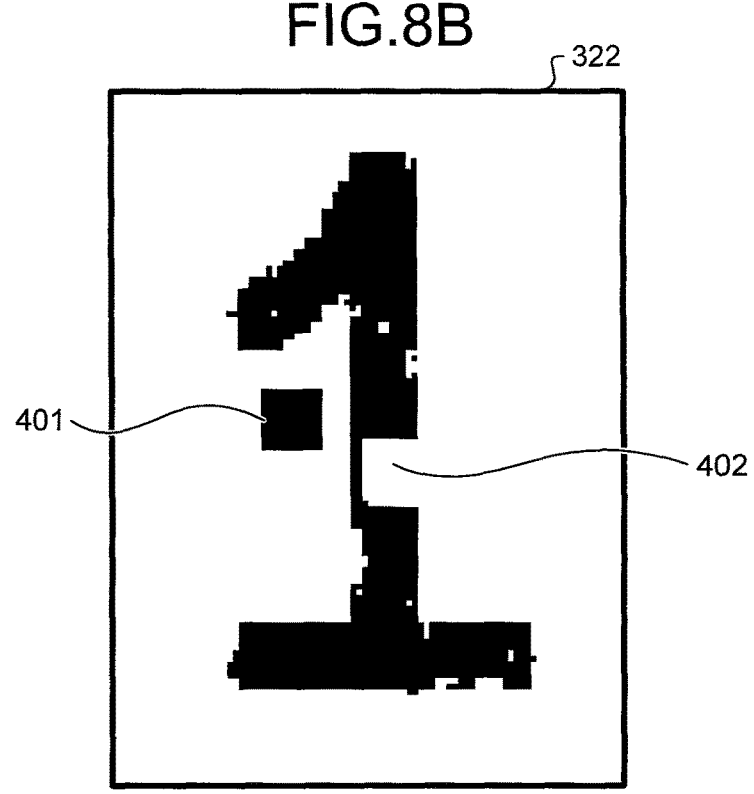

The character-background removing unit 75 performs the binarization processing to remove the noise 403a to 403d thereby generating a binary image from the background-removed image 321 (Step S16). As a result, the insignificant noise 403a to 403d remaining in the background-removed image 321 is also removed and the character image containing only the character can be acquired. FIG. 8B shows a character image 322 generated from the background-removed image 321 shown in FIG. 8A by executing the binarization processing. The character image 322 is a binary image in which the pixels constituting the background are represented with white pixels and the pixels constituting the character are represented with black pixels. In this manner, the presence of the stain 401 and the missing portion 402 becomes clear in the character image 322, and the printing inspection of the character image 322 can be performed appropriately by using this character image 322.

The printing inspection unit 76 evaluates the printing quality of the character contained in the character image 322 obtained by the character-background removing unit 75 (Step S17). As shown in FIG. 8B, the character image 322, which is obtained by removing the background design from the color input image 301 that is obtained by capturing the large-size printed object 200, is an image that allows determination of the presence of the stain 401 and the missing portion 402. The printing inspection unit 76 determines the printing quality of the character by comparing the character image 322 shown in FIG. 8B with the font image 500 shown in FIG. 6. As the printing quality, the presence of the stain 401 and the missing portion 402, printing position misalignment of a character, fading, a character width, and the like, are evaluated.

Figure 9:
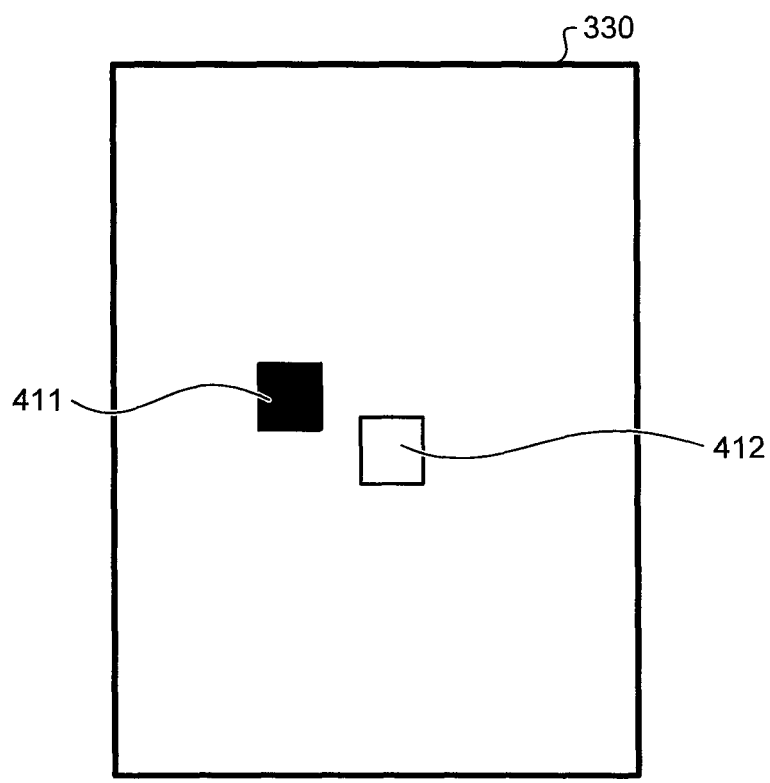
FIG. 9 is a view of a subtraction image generated from a difference between the character image and the font image.

For example, the printing inspection unit 76 generates a subtraction image from the character image 322 and the font image 500 to determine whether the stain 401 or the missing portion 402 is present. FIG. 9 shows a subtraction image 330 obtained from the character image 322 and the font image 500. In this manner, the pixels constituting the character are absent in the subtraction image 330. Moreover, a stain 411 and a missing portion 412, corresponding to the stain 401 and the missing portion 402 contained in the input image 301 shown in FIG. 4, are represented with different pixel values in the subtraction image 330. It allows differentiation between the stain 411 and the missing portion 412. Therefore, it is possible to determine whether the stain 401 or the missing portion 402 is contained in the subtraction image 330, and it is possible to evaluate the printing quality.

The step for obtaining the discriminant function by separating the pixels constituting the input image 301 into the character part and the background part is, as explained above, executed automatically after having obtained the character recognition result. However, the present embodiment is not limited to this configuration. That is, the step to obtain the discriminant function can be executed manually before or after obtaining the character recognition result. Specifically, after having obtained the character recognition result, it is allowable to manually execute only the step to separate the character part and the background part to demand the discriminant function. However, sometimes it may be difficult to obtain the character recognition result due to the influence of the background design and the like. In such a case, the discriminant function can be obtained previously by separating the character part and the background part by a manual operation before obtaining the character recognition result. After having obtained the character recognition result by applying this discriminant function, as explained above, the discriminant function can be automatically obtained and the background can be removed. Accordingly, when it is difficult to obtain the character recognition result, by previously setting the discriminant function for one character manually, a character recognition result can be obtained for all the characters other than the one character by using the manually set discriminant function, and the next step can be executed without problem. In either case, the discriminant function can be obtained by the same operation method. The operation method is explained below.

Figure 10:
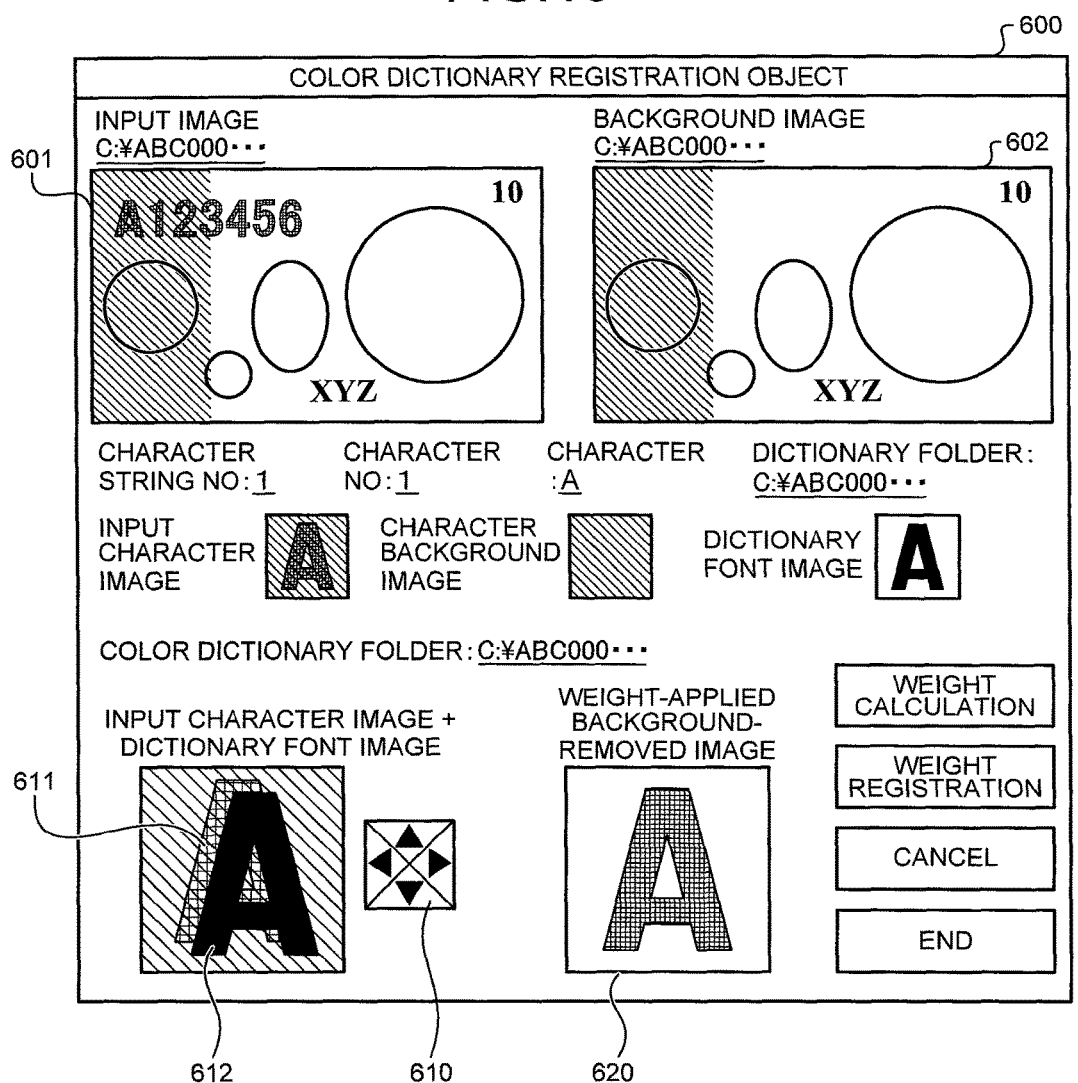
FIG. 10 is a view of an exemplary operation screen displayed when manually performing a processing to separate the character part and the background part of the input image.

FIG. 10 is a view of an exemplary operation screen displayed on the operation/display unit 50 when manually performing a processing to separate the character part and the background part of the input image. As shown in FIG. 10, an input image 601 and a background image 602 are displayed on a screen 600. The input image 601 displayed on the screen is an image of an entire fragment containing a character that is the object of the printing inspection. The background image 602 is an image of the entire fragment that does not contain the character that is the object of the printing inspection. The input image 601 and the background image 602 are previously stored in the memory 60.

The input image 601 displayed on the screen 600 is checked, and the character that is the object of the printing inspection, that is, the character that is the processing object of the process to separate into the character part and the background part, is selected. When a character string number and a character number are specified by operating the operation/display unit 50, an input character image and a character background image are displayed below the input image 601 and the background image 602 respectively. The input character image is an image obtained by cutting out from the input image 601 a partial region that contains the character specified by the character string number and the character number. The character background image is an image obtained by cutting out from the background image 602 an image of a partial region corresponding to the region of the input character image. That is, the character background image represents a state in which only the background design is present but no character is printed thereon, and the input character image represents a state in which the specified character is printed on the background design. The input character image shown in FIG. 10 is the input image mentioned above.

In the example shown in FIG. 10, because the character string number has been specified as "1", a character string "A123456" is selected from a plurality of character strings contained in the input image 601. Moreover, because the character number has been specified as "1", the first character "A" in the character string is selected. Accordingly, an input character image of the character "A" is displayed, and the character background image at the region corresponding to the region of the character "A" is displayed.

Moreover, as shown below the background image 602 on the screen 600, "A" is specified as the character, and a dictionary folder is specified. As a result, a dictionary font image corresponding to the specified character "A" is retrieved from among the dictionary font images stored in the dictionary folder and displayed. The dictionary font image shown in FIG. 10 is the font image mentioned above.

In this way, when the input character image and the dictionary font image are specified, an image obtained by overlapping the dictionary font image on the input character image is displayed in a lower-left part of the screen 600. In this state, direction buttons 610 are operated so that a position of a character 611 contained in the input character image matches with a position of a character 612 contained in the dictionary font image whereby the two characters 611 and 612 overlap each other.

After operating the direction buttons 610 and moving the character 612 contained in the dictionary font image to make the character positions of the two characters 611 and 612 overlap, a weight calculation button on the screen 600 is operated. As a result, the pixels of the input character image that are present at the position overlapping with the pixels constituting the character 612 contained in the dictionary font image are taken as the pixels of the character part, and the pixels other than those are taken as the pixels of the background part. Then, the linear distinction processing for obtaining the linear discriminant function for separating the pixels into the character part and the background part based on the respective pixel value is started, and the weights W1 to W4 in the linear discriminant function are calculated.

After calculating the weights in the linear discriminant function, the image from which the background design has been removed from the input character image by using the calculated weights is displayed on the screen 600 as a weight-applied background-removed image 620. After having confirmed in the weight-applied background-removed image 620 that the background has been removed, a weight registration button is operated. As a result, information about the calculated weights W1 to W4 is stored in the memory 60. In this state, an end button is operated. As a result, the next step, that is, the character recognition by the character recognition unit 74 and the printing inspection by the printing inspection unit 76, are performed by using the stored weights W1 to W4. The information about the weights W1 to W4 is managed in the memory 60 as color dictionary data. The information about the weights W1 to W4 is stored in association with a kind of fragment, positional information of the character in the fragment, and the like. The color dictionary data is stored in a specified color dictionary folder.

When each of the characters constituting the character string is printed with a different color, the color of the character part may change depending on the printing conditions. Specifically, for example, in a serial number of some available banknotes, a character at a digit at one end of the serial number is printed in red, a character in a digit at the other end is printed in green, and the characters in digits in between are printed in a color that is a mixture of red and green. Such a printing scheme is generally called rainbow printing. In the printed material printed with the rainbow printing, the color of the characters in the digits in between may change depending on the mixing state of the red ink and the green ink.

The character background removing apparatus according to the present embodiment can handle such a situation. A concrete explanation has been given below assuming that the color of a character in central digit, i.e., the fourth digit from left, in a seven-digit character string exemplified in FIG. 10 may change.

Figure 11:
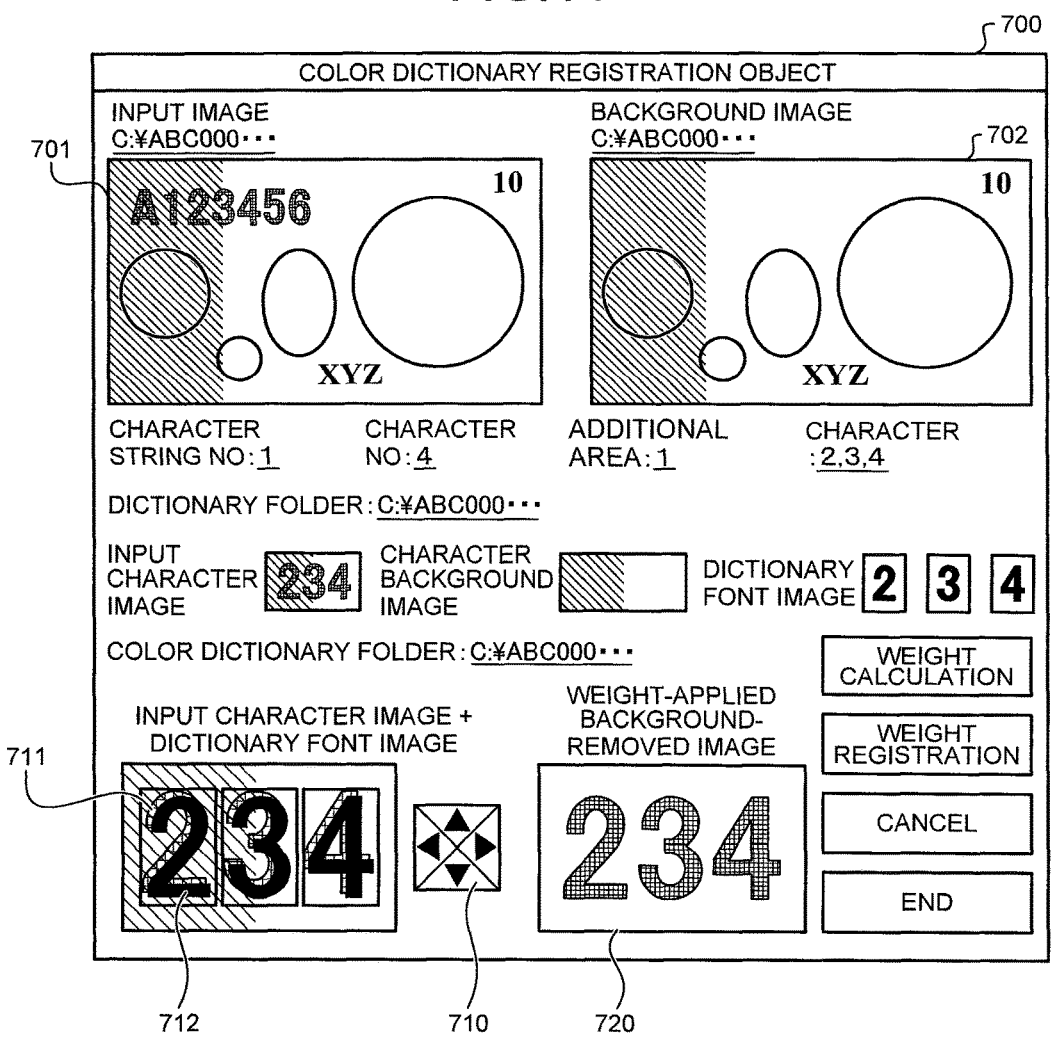
FIG. 11 is a view of another exemplary operation screen displayed when manually performing a processing to separate the character part and the background part of the input image.

FIG. 11 is a view of an exemplary operation screen displayed on the operation/display unit 50 when manually performing a processing to separate the character part and the background part of an input image. As shown in FIG. 11, an input image 701 and a background image 702 are displayed on a screen 700. The input image 701 displayed on the screen is an image of an entire fragment containing a character that is the object of the printing inspection. The background image 702 is an image of the entire fragment that does not contain the character that is the object of the printing inspection. The input image 701 and the background image 702 are previously stored in the memory 60.

The input image 701 displayed on the screen 700 is checked, and the character that is the object of the printing inspection, that is, the character that is the processing object of the process to separate into the character part and the background part, is selected. In the example shown in FIG. 11, because the character string number has been specified as "1", a character string "A123456" is selected from a plurality of character strings contained in the input image 701. Moreover, because the character number has been specified as "4", a character "3" in the fourth digit from left in the character string is selected. Moreover, because an additional area has been specified as "1", one character on the left and one character on the right of the character "3" at the fourth digit are selected. As a result, as shown in FIG. 11, an input character image "234" and a character background image at the corresponding region of this input character image are displayed on the screen 700.

The additional area specifies how many characters on the left and the right of the character at the fourth digit that is the processing object are to be taken as the processing objects. When the additional area is set to "2", for example, on the screen 700 shown in FIG. 11, the input image will be "12345". A desired number "n" that does not exceed a range of the number of characters in the character string can be specified as the additional area. In the example shown in FIG. 11, "n" can be set to any number among 1, 2, 3 with the fourth digit as the center. The number to be specified as the additional area can be specified while considering an area in which the color may change.

Moreover, as shown below the background image 702 in FIG. 11, "2", "3", "4" are specified as the characters, and a dictionary folder is specified. As a result, the dictionary font images of the characters in the specified character string "234" are displayed from among the dictionary font images stored in the dictionary folder.

In this way, when the input character image and the dictionary font images are specified, an image obtained by overlapping the dictionary font images on the input character image is displayed in a lower-left part of the screen 700. In this state, direction buttons 710 are operated so that character positions of a character string 711 of "234" contained in the input character image matches with character positions of a character string 712 of "234" contained in the dictionary font images whereby the two character strings 711 and 712 overlap each other.

After operating the direction buttons 710 and moving the character string 712 contained in the dictionary font images to make the character positions of the two character strings 711 and 712 overlap, a weight calculation button on the screen 700 is operated. As a result, the pixels of the input character image that are present at the position overlapping with the pixels constituting the character string 712 contained in the dictionary font images are taken as the pixels of the character part, and the pixels other than those are taken as the pixels of the background part. Then, the linear distinction processing for obtaining the linear discriminant function for separating the pixels into the character part and the background part based on the respective pixel values is started, and the weights W1 to W4 in the linear discriminant function are calculated. In the present embodiment, the act of operating a button on a screen includes pressing a button or touching a button on a touch panel-type liquid crystal display.

After calculating the weights in the linear discriminant function, the image from which the background design has been removed from the input character image by using the calculated weights is displayed on the screen 700 as a weight-applied background-removed image 720. After having confirmed in the weight-applied background-removed image 720 that the background has been removed, a weight registration button is operated. As a result, information about the calculated weights W1 to W4 is stored in the memory 60. In this state, an end button is operated. As a result, the next step, that is, the character recognition by the character recognition unit 74 and the printing inspection by the printing inspection unit 76, are performed by using the stored weights W1 to W4. The information about the weights W1 to W4 is managed in the memory 60 as the color dictionary data. The information about the weights W1 to W4 is stored in association with a kind of fragment, positional information of the character in the fragment, and the like. The color dictionary data is stored in a specified color dictionary folder.

After specifying the character string "234", each of the characters forming this character string can be treated equally, or a different weight can be applied to each of the characters in the character string. For example, a higher weight can be applied to the character "3", which is the processing object, than the character "2" on the left and the character "4" on the right of the processing object. By doing this, a linear discriminant function that puts more weight on the pixel values of the pixels that constitute the character "3" can be calculated.

Figure 12:
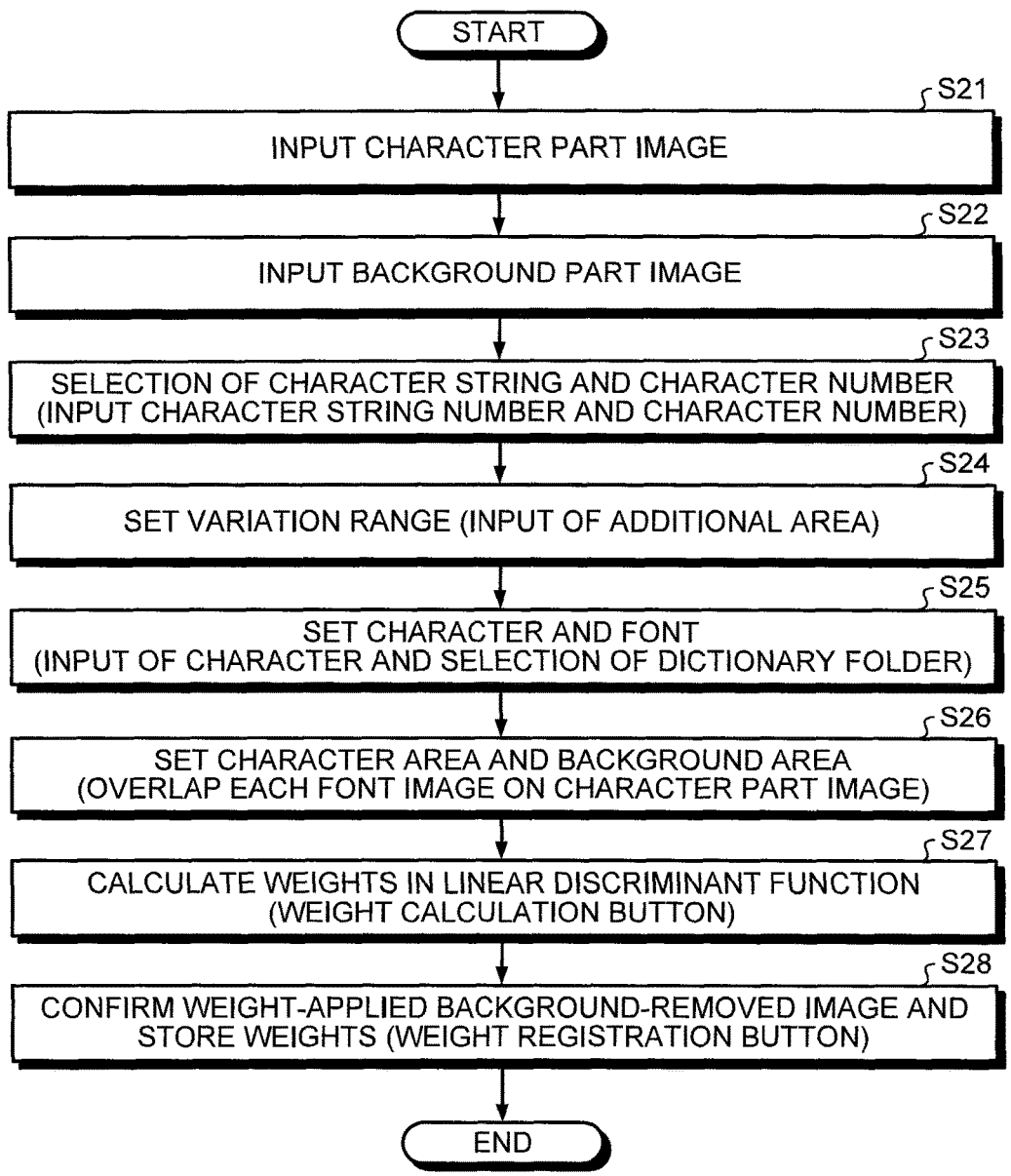
FIG. 12 is a flowchart indicating a flow of processing for registering a linear discriminant function.

In this manner, before performing the character recognition, processing to generate the linear discriminant function for separating the character part and the background part can be performed on the screen 700 shown in FIG. 11. FIG. 12 is a flowchart indicating a flow of processing for registering the linear discriminant function. As shown in FIG. 11, at first, the input image 701 is input as a character part image (Step S21) and the background image 702 is input as a background part image (Step S22).

The input image 701 displayed on the screen 700 is checked, and the character string number and the character number are specified to select the character that is the processing object of the processing to separate into the character part and the background part (Step S23). Moreover, the number to be specified as the additional area is input to specify a range of the number of digits at which the color of the character may change (Step S24). Then, after selecting the character string that is the processing object by using the input image 701, to specify each of the characters constituting this character string and the font thereof, each of the characters constituting the character string is input on the screen 700 and a dictionary folder is selected (Step S25).

Subsequently, a character part and a background part are set (Step S26). That is, a position is specified on the screen 700 at which the character string contained in the input character image selected from the input image 701 and the dictionary font images of the character string set in Steps S23 to S25 overlap. Then, after setting the character part and the background part by adjusting the position of the dictionary font image on the input character image containing the character string and specifying the character part, the weight calculation button is operated to calculate the weights W1 to W4 in the linear discriminant function (Step S27).

After calculating the weights in the linear discriminant function, the image from which the background design has been removed from the input character image is displayed as the weight-applied background-removed image 720. After having confirmed in the weight-applied background-removed image 720 that the background has been removed, the weight registration button is operated. As a result, information about the calculated weights W1 to W4 is stored in the memory 60 (Step S28).

An example has been shown in FIG. 12 in which the additional area is specified when the color of the character constituting the character string changes. Besides this, for example, if a printing position of the character, a printing position of the background design, or the like changes, i.e., when there is printing misalignment between the positions of the background and the character, the linear discriminant function can be obtained after specifying the additional area. By doing so, the effect of the printing misalignment can be reduced.

Figure 13:
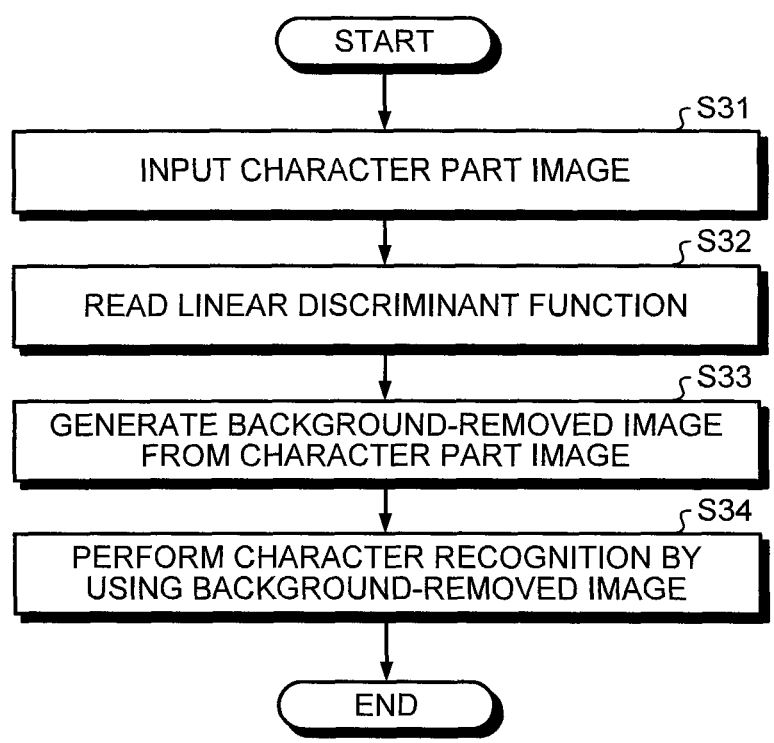
FIG. 13 is a flowchart indicating a flow of character recognition processing that employs the linear discriminant function prepared previously.

By storing the information about the linear discriminant function into the memory 60 in this manner, the character recognition processing can be performed by reading the stored information. FIG. 13 is a flowchart indicating a flow of the character recognition processing that employs the linear discriminant function prepared previously in the memory 60. The character part image is input (Step S31), the linear discriminant function prepared previously is read (Step S32), the background-removed image is generated from the character part image by using the read linear discriminant function (Step S33), and the character recognition processing is performed by using the background-removed image (Step S34).

It is not necessary that the method for removing character background according to the present embodiment is used stand-alone. For example, a conventional method can be used when the background of the character can be removed in character units, character string units, fragment units, and large-size printed object units by using the conventional color dropout processing, and the method for removing character background according to the present embodiment can be used only when the background of the character cannot be appropriately removed with the conventional method. Because the details of the character and the background that are the objects of the printing evaluation are previously known when performing the printing evaluation, which method is to be used to remove the background of the character can be selected depending on the character and the background.

Moreover, the present embodiment explains an example of removing the background design present in the background of a number or an English alphabet; however, the character according to the present embodiment is not limited to these. For example, the character can be a Hiragana character, a Katakana character, a kanji (Chinese) character, and the like, or the character can be a symbol.

As mentioned above, according to the present embodiment, even if the printed object has a character printed in the same color as that of a background design, the printed object has a character string of which each character is printed in different colors, the printed object contains a character with a background design having a plurality of colors, and the like, a character image obtained by removing a pattern and the like present in the background of the character from the color input image can be acquired. When removing the background, because not only information about pixels that constitute the character is left behind unremoved, but also information about a missing portion of the character, a stain of the ink with which the characters are printed, and the like can be left behind unremoved, a character image that can be used in the inspection of the printing quality can be acquired.

Second Embodiment

Subsequently, a method and an installation adjustment chart of a line camera are explained. The method and the installation adjustment chart of a line camera according to the present embodiment are, for example, intended to adjust an installation position of a line camera used to capture a large-size printed object that is transported by an inspection drum arranged in a large-scale printing machine to check a printing quality of the large-size printed object that is printed by the printing machine. The installation position is defined by a position and an angle of the line camera with respect to the inspection drum. The large-size printed object is rotated and transported in an imaging range of the line camera by the rotation of the cylindrical inspection drum. An image of the entire large-size printed object is acquired from line data captured line by line by the line camera by scanning the rotated and transported large-size printed object.

Figure 14:
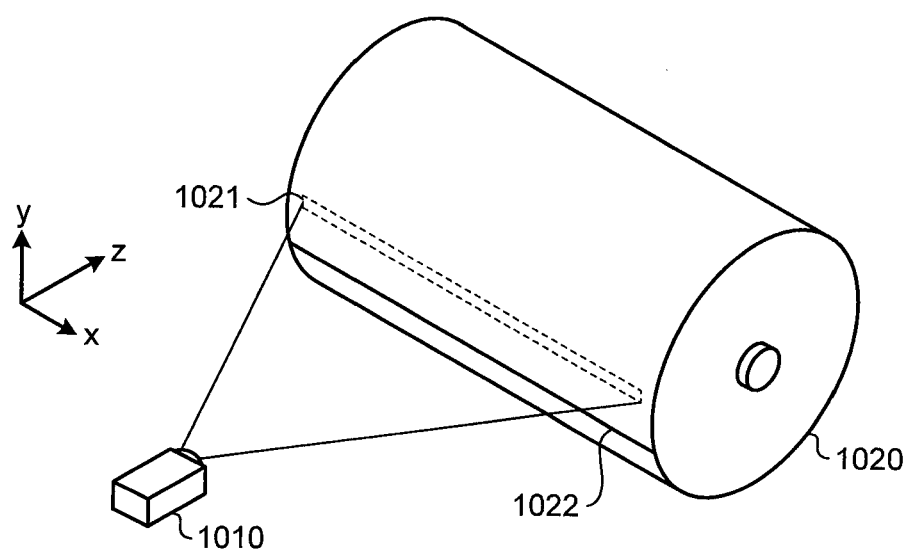
FIG. 14 is a schematic diagram indicating a positional relationship between a line camera and an inspection drum according to a second embodiment.

FIG. 14 is a schematic diagram indicating a positional relationship between a line camera 1010 and an inspection drum 1020. In FIG. 14, the x-axis direction corresponds to the horizontal direction and the y-axis direction corresponds to the vertical direction. Moreover, the line camera 1010 is installed so that an optic axis direction thereof corresponds to the z-axis direction when installed at a normal installation position. The cylindrical inspection drum 1020 is rotatably supported by a rotation axis that is arranged parallel to the x-axis. The cylindrical inspection drum 1020 is rotationally driven by a not-shown inspection-drum driving unit. When the inspection drum 1020 rotates, a large-size printed object fixed to an outer peripheral surface of the inspection drum 1020 passes an imaging region 1021, shown with a dashed line in FIG. 14, of the line camera 1010 at a speed of 4 m/s, for example.

The line camera 1010 includes an imaging device in which a plurality of light receiving elements of each of the RGB colors is arranged horizontally in one line or in several lines. The line camera 1010 acquires R (red) line data, G (green) line data, and B (blue) line data by capturing an image of the large-size printed object line by line. The imaging device of the line camera 1010 has, for example, 8192 pixels in one line.

The line camera 1010 is supported by a not-shown camera holder in the installation position thereof adjustable manner. Specifically, the line camera 1010 is supported by the camera holder so as to be movable parallel to each of the x-axis, the y-axis, and the z-axis. Moreover, the line camera 1010 is rotatable about each of the x-axis, the y-axis, and the z-axis. The installation position of the line camera 1010 can be adjusted and the line camera 1010 can be fixed at the normal installation position by an adjustment mechanism of the camera holder. Because a conventional device can be used as the camera holder that adjusts the installation position of the line camera 1010 by the movement along the three axes and the rotation around the three axes, the detailed explanation thereof has been omitted. The adjustment of the installation position of the line camera 1010 can be performed by manually operating the adjustment mechanism of the camera holder, or can be performed by controlling a motor and the like that drives the adjustment mechanism.

To accurately capture an image of the large-size printed object that is transported by the rotation of the inspection drum 1020, the installation position of the line camera 1010 is adjusted so that the optic axis direction thereof matches with the z-axis. Moreover, the installation position of the line camera 1010 is adjusted so that a direction of alignment of the light receiving elements included in the line camera 1010, i.e., the line direction (a scan line direction) of the line data, matches with the x-axis. Besides, any position misalignment or inclination of the line camera 1010 in various directions is adjusted and corrected. The adjustment of the installation position is performed while checking a signal waveform obtained by capturing with the line camera 1010 an installation adjustment chart that is fixed to the inspection drum 1020. At first, a system configuration for adjusting the installation position of the line camera 1010 is explained.

Figure 15:
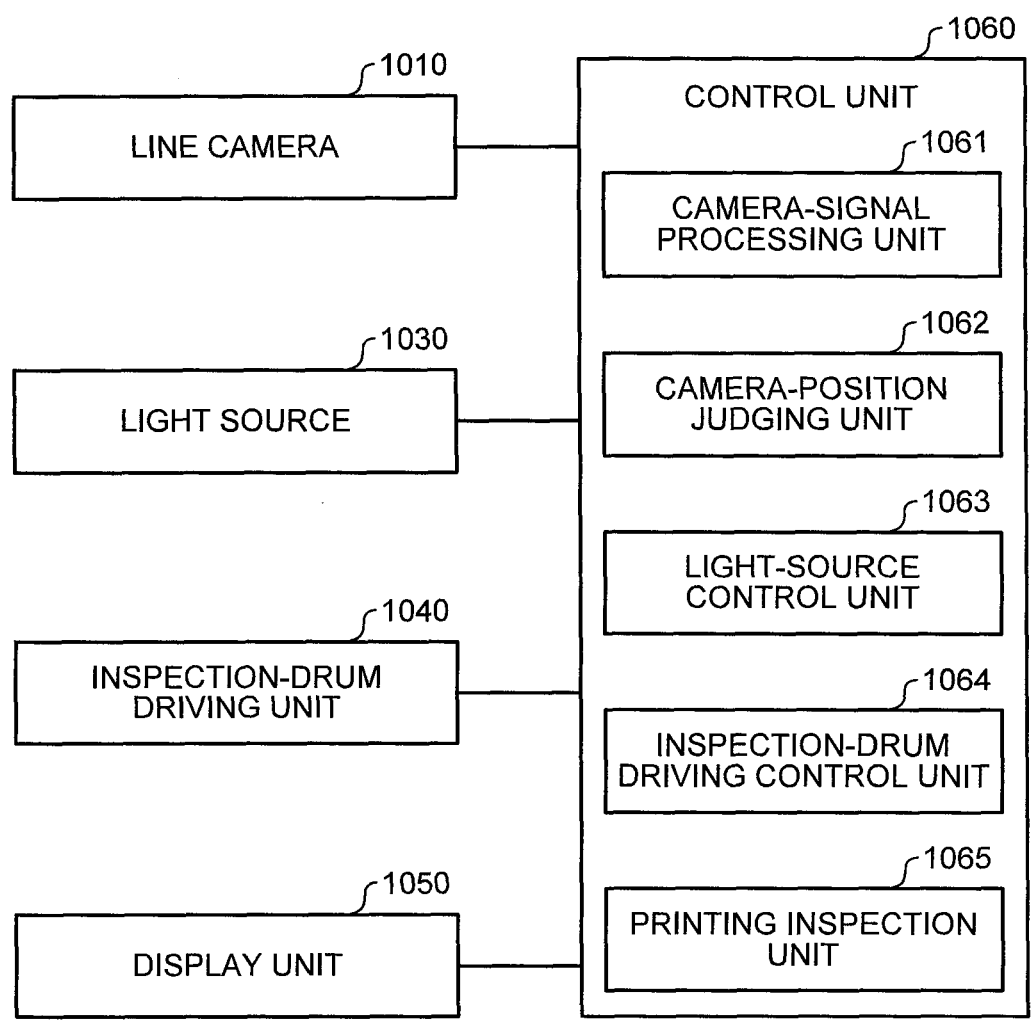
FIG. 15 is a block diagram of a general configuration of a printing machine system including the line camera.

FIG. 15 is a block diagram of a general configuration of a printing machine system including the line camera 1010. The printing machine system includes, besides the line camera 1010 shown in FIG. 14, a light source 1030, an inspection-drum driving unit 1040, a display unit 1050, and a control unit 1060.

The light source 1030 illuminates the imaging region 1021 of the line camera 1010 on the inspection drum 1020. If a partial region that reflects the irradiated light, such as a hologram or a security thread, is present in fragments of the large-size printed object, and the light reflected from such a partial region directly enters the line camera 1010, a brightness difference between this partial region and the other region in the fragment becomes large. It causes so-called blown out highlights or blocked up shadows, and a high accuracy image of the entire large-size printed object cannot be captured. Therefore, the light source 1030 is installed so that the light reflected from the large-size printed object does not directly enter the line camera 1010.

Figure 16A:
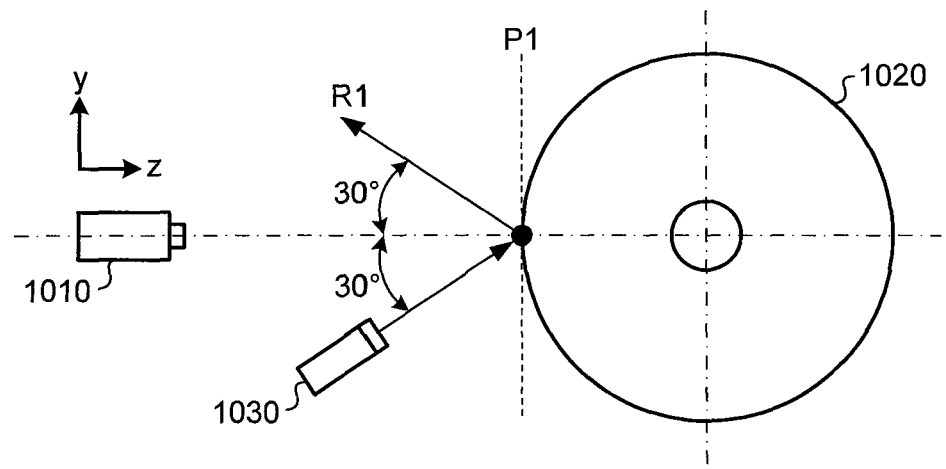
FIGS. 16A and 16B are schematic diagrams for explaining installation positions of a light source.
Figure 16B:
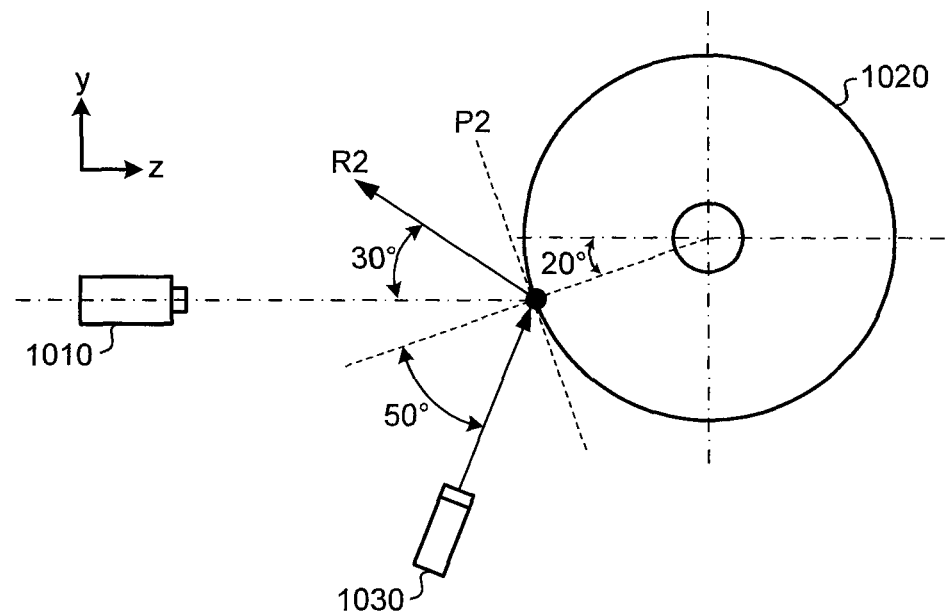

FIGS. 16A and 16B are schematic diagrams indicating the installation positions of the light source 1030. As shown in FIG. 16A, when the rotation axis of the inspection drum 1020 is parallel to the x-axis and the optic axis of the line camera 1010 is parallel to the z-axis, and the positional relationship is such that the rotation axis of the inspection drum 1020 and the optic axis of the line camera 1010 fall on the same measurement plane that is parallel to the xz-plane, the light source 1030 is installed at a position where it makes a predetermined angle with respect to the measurement plane. Specifically, as shown in FIG. 16A, the light source 1030 is installed so that an angle between the measurement plane and each of an incident light output from the light source 1030 and a reflected light R1 reflected by the inspection drum 1020, i.e., an angle of incidence and an angle of reflection of the light at a reflection plane 21 on the inspection drum 1020, are both 30 degrees. FIG. 16B shows a case in which the line camera 1010 is translational moved in the negative y-axis direction from its position shown in FIG. 16A. In this manner, even if the measurement plane including the optic axis of the line camera 1010 has been shifted with respect to the rotation axis of the inspection drum 1020, the light source 1030 is installed so that a reflected light R2 from the inspection drum 1020 makes a predetermined angle with the measurement plane. In the example shown in FIG. 16B, a reflection plane P2 is formed to include a point of the outer peripheral surface of the inspection drum 1020 that makes an angle of 20 degrees with the xz-plane. For example, by installing the light source 1030 so that the angle of incidence of the light on the reflection plane P2 is 50 degrees, the angle between the measurement plane of the line camera 1010 and the reflected light R2 can be made 30 degrees. In this manner, the angle between the reflected lights R1 and R2 and the measurement plane can be set to around 30 degrees by setting the position of the light source 1030 based on the positions of the reflection planes P1 and P2 on the outer peripheral surface of the inspection drum 1020 and the measurement plane. This allows an image of the large-size printed object on the inspection drum 1020 to be captured with the line camera 1010 without being affected by the reflected lights R1 and R2.

The inspection-drum driving unit 1040 shown in FIG. 15 rotationally drives the inspection drum 1020 by using a motor and the like. Moreover, the inspection-drum driving unit 1040 detects a rotation angle and a rotation position of the inspection drum 1020 by using a rotary encoder and the like. As shown in FIG. 14, the outer peripheral surface of the inspection drum 1020 is provided with a mark 1022 indicating a position for fixing the installation adjustment chart. When starting the installation adjustment of the line camera 1010, an upper edge of the installation adjustment chart is matched with the mark 1022 on the inspection drum 1020, the right and left edges of the installation adjustment chart are matched with the right and left edges of the inspection drum 1020, and an installation adjustment chart 1070 is fixed to the inspection drum 1020 in this state. Subsequently, the inspection-drum driving unit 1040 is controlled to rotate the inspection drum 1020 to a predetermined rotation position so that the installation adjustment chart 1070 and the line camera 1010 are at a predetermined position where they are face-to-face opposite to each other. The rotation of the inspection drum 1020 is stopped, and the inspection drum 1020 is fixed at this predetermined rotation position.

The display unit 1050 is a display device, such as a liquid crystal display, that displays various information. The information displayed on the display unit 1050 includes a signal obtained by the line camera 1010 by capturing the installation adjustment chart that has been fixed to the inspection drum 1020, information about such a signal, and the like.

The control unit 1060 includes a camera-signal processing unit 1061, a camera-position judging unit 1062, a light-source control unit 1063, an inspection-drum driving control unit 1064, and a printing inspection unit 1065. The camera-signal processing unit 1061 acquires an imaging signal from the line camera 1010. The camera-position judging unit 1062 judges an installation status of the line camera 1010 based on the imaging signal acquired by the camera-signal processing unit 1061, and causes the display unit 1050 to display a judgment result. The light-source control unit 1063 adjusts an illuminance of the light output from the light source 1030 depending on a temperature variation and a degradation state of the light source 1030. The inspection-drum driving control unit 1064 controls the inspection-drum driving unit 1040 to perform rotation control of the inspection drum 1020, control of the rotation position of the inspection drum 1020 by stopping the inspection drum 1020, fixing of the stopped inspection drum 1020, and the like. Moreover, the inspection-drum driving control unit 1064 recognizes the rotation position of the inspection drum 1020. The camera-signal processing unit 1061 acquires the line data by scanning the large-size printed object line by line from the rotation position of the inspection drum 1020 recognized by the inspection-drum driving control unit 1064.

Figure 17A:
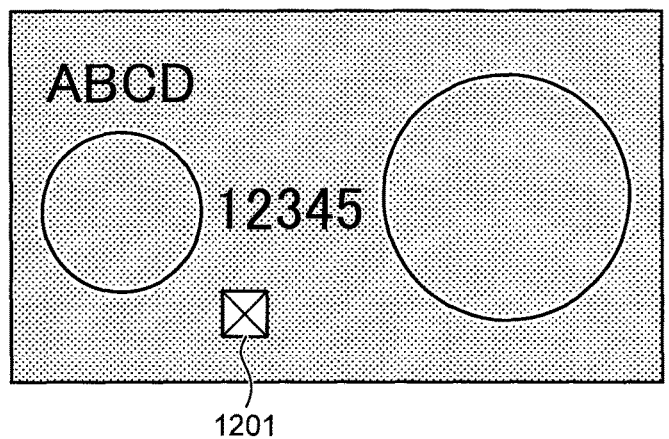
FIGS. 17A and 17B are schematic diagrams for explaining a calibration method of illuminance variation of the light source used to illuminate a large-size printed object and setting of a threshold value to be used in printing evaluation.
Figure 17B:
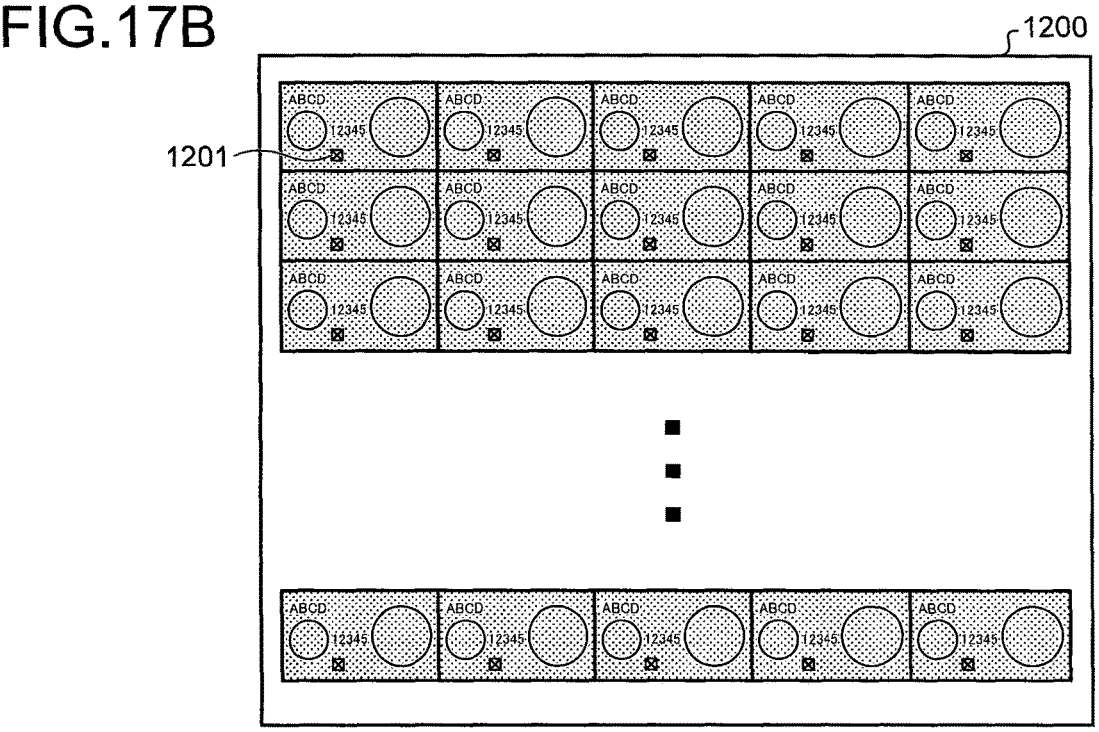

The printing inspection unit 1065, after having completed the installation adjustment of the line camera 1010, checks the printing quality of each of the fragments constituting the large-size printed object based on the image of the large-size printed object captured by the line camera 1010. Moreover, the printing inspection unit 1065 corrects an illuminance variation of the light source 1030 when performing the printing inspection. FIGS. 17A and 17B are schematic diagrams for explaining a calibration method of illuminance variation of the light source 1030 used to illuminate the large-size printed object and setting of a threshold value to be used in the printing evaluation.

For example, when evaluating a character density of the printed object shown in FIG. 17A in the printing inspection, the evaluation is performed after correcting the character density depending on the light concentration so that the result is not affected by the illuminance variation of the light source 1030. Specifically, the printing inspection unit 1065 acquires a brightness value in a predetermined partial area 1201 on each of the fragment images of the printed object, and evaluates the character density after correcting the character density obtained from the fragment image based on the acquired brightness value. When performing the printing inspection of a large-size printed object 1200 shown in FIG. 17B, the partial area 1201 in each of the fragments constituting the large-size printed object 1200 is detected, and each of the fragment images is corrected based on a brightness value of the corresponding partial area 1201. This allows the printing quality of each of the fragments to be evaluated with a high accuracy. The partial area 1201 to be used for such a correction is previously set depending on a design or a pattern in the fragment. For example, a mark contained in each of the fragments to detect a position of each of the fragments, a partial area having a white background, and the like, where the printing is performed stably can be used as the partial area 1201.

Moreover, the printing inspection unit 1065, when evaluating the printing quality of each of the fragments, can change the threshold value, which is to be used as a reference, from fragment to fragment. For example, when evaluating the position misalignment of a character in the printed object shown in FIG. 17A, the printing inspection unit 1065 evaluates the position misalignment of the character while changing a tolerance value of the position misalignment of the character depending on the position of the fragment in the large-size printed object 1200. While printing and transportation are repeated in a printing machine, a part of a large-size paper may expand and another part may contract. Accordingly, a shape or a printed state of a fragment in the center and a fragment at the periphery of the same large-size printed object may vary. In such instances, by setting the threshold value previously depending on the position in the large-size printed object, the printing quality of each of the fragments can be evaluated depending on the position thereof in the large-size printed object. Besides the tolerance value of the position misalignment, a tolerance value to be used when performing each of the printing evaluation of a missing portion, stain, color misalignment, ink density, and the like, can be changed depending on the position of the fragment.

Figure 18:
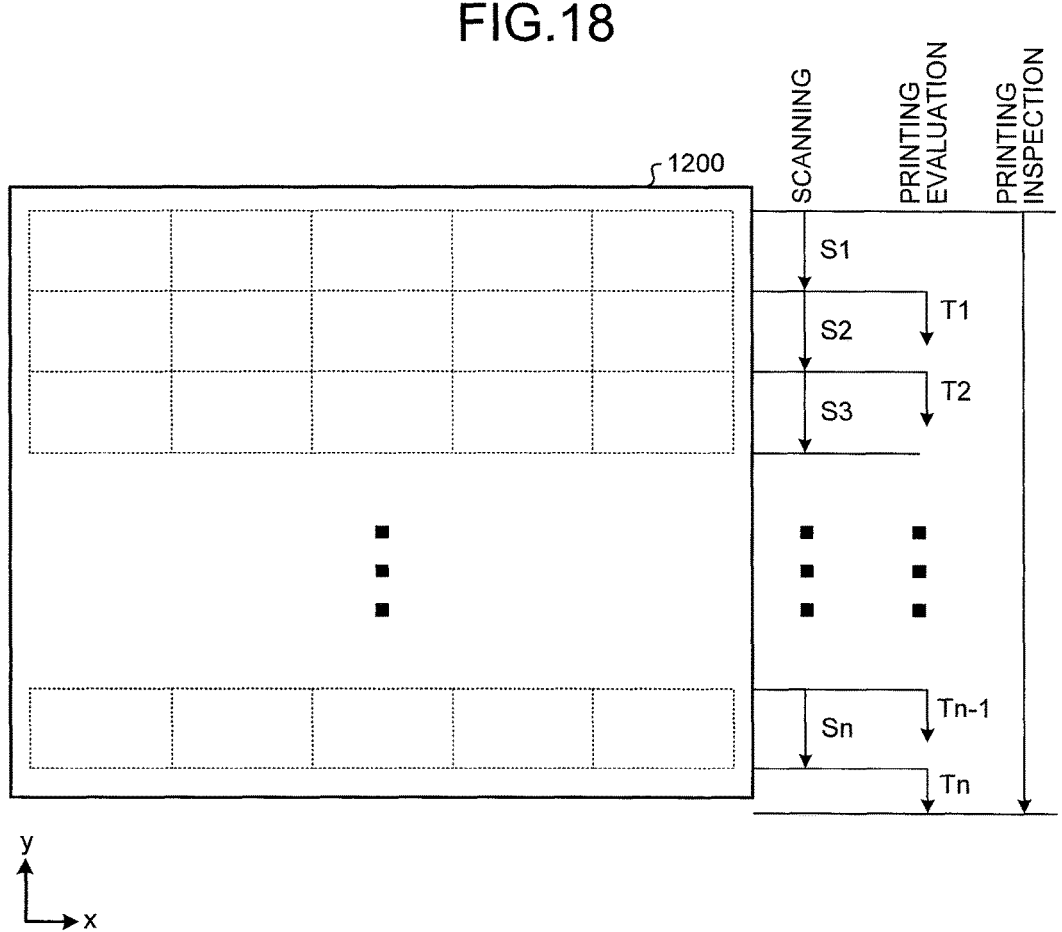
FIG. 18 is a schematic diagram for explaining parallel processing performed on the large-size printed object.

In the printing machine system, to complete the printing inspection by the printing inspection unit 1065 in a short time, the scanning processing and the printing evaluation processing are performed in parallel. The scanning processing is a processing to scan the large-size printed object 1200 with the line camera 1010 thereby acquiring the fragment images, while the printing evaluation processing is a processing to evaluate the printing quality. Before performing the printing evaluation processing, image processing involving density correction and the like of each of the fragments may be performed as needed. FIG. 18 is a schematic diagram for explaining a parallel processing performed on the large-size printed object 1200. The large-size printed object 1200 containing a plurality of fragments arranged in a matrix of 5 rows and "n" is shown in the left side in FIG. 18. A relation between times S1 to Sn necessary for the scanning processing of each of the lines of the large-size printed object 1200, times T1 to Tn necessary for the printing evaluation processing of each of the lines, and an inspection time necessary for the printing inspection of the entire large-size printed object 1200 is shown in the right side in FIG. 18. The processing time shown in the right side of FIG. 18 indicates that the time elapses as one goes downward. For example, FIG. 18 shows that the scanning processing for the 1-st line is completed after the elapse of the time S1 from the start of the scanning processing, and that the printing evaluation processing for the 1-st line is started together with the start of the scanning processing for the 2-nd line.

The camera-signal processing unit 1061 scans the large-size printed object 1200, which passes the imaging region 1021 by the rotation of the inspection drum 1020, with the line camera 1010, line by line, from an upper edge of the large-size printed object 1200 thereby acquiring the line data. When the scanning processing for the 1-st line is completed within the time S1 from the start of the scan, the scanning of the fragments in the 2-nd line is started successively. Thus, the total time necessary to complete the scanning of all the fragments of the 5 rows and "n" lines contained in the large-size printed object 1200 is the sum of the times S1 to Sn.

After the camera-signal processing unit 1061 completes the scanning of the fragments in the 1-st line, the printing inspection unit 1065 starts the printing evaluation processing. The printing evaluation processing of all the fragments in the 1-st line is completed within the time T1. Moreover, at the instant the camera-signal processing unit 1061 has completed the scanning of the fragments of the 2-nd line, the printing inspection unit 1065 starts the printing evaluation processing and completes the printing evaluation processing of all the fragments of the 2-nd line within the time T2. As a result, the printing evaluation processing of the fragments of all the "n" lines on the large-size printed object 1200 can be completed after elapse of the time Tn from the completion of the scanning of the n-th line by the camera-signal processing unit 1061. That is, after elapse of the time (sum of the times S1 to Sn) necessary for scanning the entire large-size printed object 1200, the printing inspection of the entire large-size printed object 1200 can be completed at the instant the time (Tn) necessary for the printing evaluation processing of the fragments of the last line has elapsed. The printing evaluation processing is performed in parallel depending on the processing capacity of the printing inspection unit 1065. For example, when five fragments are present in one line, the printing evaluation processing of each of the fragments in the one line is performed in parallel. As a result, the printing evaluation processing of all the five fragments is completed in the processing time necessary for processing one fragment.

Subsequently, the installation adjustment chart used to adjust the installation position of the line camera 1010 will be explained. FIGS. 19A to 19C are views indicating the installation adjustment chart 1070. FIG. 19A is a view that schematically shows the configuration of the installation adjustment chart 1070, FIG. 19B is a view of an actual configuration thereof, and FIG. 19C is an enlarged view of a partial region 1072 shown in FIG. 19B.

As shown in FIG. 19A, the installation adjustment chart 1070 includes perpendicular lines 1073a and 1073b at both the ends thereof, a perpendicular line 1071 at a center with respect to the perpendicular lines 1073a and 1073b, rectangular upper patterns 1080a to 1080d and rectangular lower patterns 1081a to 1081e shown with broken lines, and a rectangular region 1082 shown with an hatched line pattern.

The upper patterns 1080a to 1080d and the lower patterns 1081b to 1081d are arranged alternately while shifting them in the y-axis direction. The lower patterns 1081a and 1081e on both the outer sides have a smaller width in the x-axis direction than the other patterns 1080a to 1080d and 1081b to 1081d. Moreover, the center position in the x-axis direction of the lower central pattern 1081c matches with the position of the line 1071.

The upper patterns 1080a to 1080d and the lower patterns 1081a to 1081e are arranged in such a positional relationship that lower partial horizontal regions of the upper patterns 1080a to 1080d and upper partial horizontal regions of the bottom patterns 1081a to 1081e overlap along the y-axis.

The rectangular region 1082 having a width L3 in the y-axis direction is formed by this overlap. That is, the lower partial horizontal regions of the upper patterns 1080a to 1080d and the upper partial horizontal regions of the bottom patterns 1081a to 1081e are continuous in the x-axis direction and form the rectangular region 1082.

Each of the patterns 1080a to 1080d and 1081a to 1081e is a line pair pattern formed by alternative white and black vertical lines. Specifically, as shown in FIG. 19B, each of the patterns 1080a to 1080d and 1081a to 1081e is formed by arranging on a white background a plurality of black lines (vertical lines) at a predetermined interval in the x-axis direction. The black lines have a predetermined length and they are parallel to the y-axis.

For example, as shown in FIG. 19C, the pattern 1080a has a length L2=100 mm in the x-axis direction, contains 100 black lines at a pitch of 1 mm on the white background. Moreover, only the black lines at both the ends are drawn with thick lines. For example, the thick lines at both the ends are drawn so that they have a width of 1 mm and the other thin lines are drawn so that they have a width of 0.5 mm. It is sufficient that the width in the y-axis direction of the pattern 1080a, i.e., the length in the y-axis direction of each of the lines forming the pattern 1080a, is about 20 mm, for example. The lines 1073a and 1073b at both the ends of the installation adjustment chart 1070, and the central line 1071 are drawn with thick lines like the lines at both the ends of the patterns.

As shown in FIG. 19C, the pitch of the lines forming each of the patterns is maintained even between the adjacent patterns that are arranged by shifting in the y-axis direction. Specifically, when the lines of each of the patterns are drawn at the pitch of 1 mm, an interval between the rightmost line of the lower pattern and the leftmost line of the upper pattern in the x-axis direction is 1 mm, and an interval between the rightmost line of the upper pattern and the leftmost line of the lower pattern in the x-axis direction is also 1 mm. As a result, the rectangular region 1082 of the width L3 shown with the hatched line pattern in FIG. 19A is a continuous region in which, on a white background, black lines parallel to the y-axis and having the length L3 are arranged horizontally at a pitch of 1 mm. Moreover, in the rectangular region 1082, the lines at both the ends of each of the patterns and the line 1071 at the center of the installation adjustment chart 1070, and the lines 1073a and 1073b at both the ends of the installation adjustment chart 1070 are drawn with thick lines allowing differentiation thereof from the other lines.

In the installation adjustment chart 1070, the black lines continue horizontally at a predetermined interval only in the rectangular region 1082. Above the rectangular region 1082, the black lines exist only in the patterns 1080a to 1080d. Below the rectangular region 1082, the black lines exist only in the patterns 1081a to 1081e.

The width L3 of the rectangular region 1082 is set to an allowable error in the installation position of the line camera 1010. For example, when the resolution of the line camera 1010 is 0.1 mm per pixel and the allowable error in the installation position is 1.2 mm, which corresponds to 12 pixels, then the width L3 is set to 1.2 mm. Moreover, a length L1 shown in FIG. 19A is set to, for example, 819.2 mm for the line camera 1010 having 8192 pixels. In this manner, because the black lines on the white background continue horizontally in the rectangular region 1082 having the width L3 so that one black line corresponds to one pixel of the line camera 1010, an abnormality of the light receiving element of the line camera can be determined on a pixel-by-pixel basis.

The values mentioned herein are exemplary. The values of L1, L2, L3, the pitch of the lines, the thickness of the lines, and the like, can be determined appropriately based on the width of the large-size printed object in the x-axis direction, performance of the line camera 1010, inspection performance demanded in the printing inspection, and the like. Moreover, the parameters L1 to L3 can be defined, besides by using the length, by using number of pixels. For example, depending on the resolution of the line camera 1010, L1 can be set as the total length for all the pixels, L2 can be set as the total length of 1000 pixels, and L3 can be set as the total length of 10 pixels.

As shown in FIG. 14, the mark 1022 used in fixing the installation adjustment chart 1070 is arranged on the outer peripheral surface of the inspection drum 1020. Before starting the installation adjustment of the line camera 1010, the upper edge of the installation adjustment chart is matched with the mark 1022 on the inspection drum 1020 and the right and left edges of the installation adjustment chart are matched with the right and left edges of the inspection drum 1020, and the installation adjustment chart 1070 is fixed to the inspection drum 1020 in this state. In this state, the inspection drum 1020 is rotated to a predetermined rotation position and fixed there. Specifically, the inspection-drum driving unit 1040 is controlled by the inspection-drum driving control unit 1064, as shown in FIGS. 16A and 16B, and the inspection drum 1020 is fixed after adjusting the rotation position of the inspection drum 1020 so that the installation adjustment chart 1070 on the inspection drum 1020 and the line camera 1010 are face-to-face opposite to each other in the reflection planes P1 or P2 on the inspection drum 1020. In this state, an installation adjustment operation of the line camera 1010 is started.

When capturing of an image of the installation adjustment chart 1070 with the line camera 1010 is started, an imaging signal acquired by the camera-signal processing unit 1061 is displayed on the display unit 1050. FIGS. 20A and 20B are views indicating a relation between the installation adjustment chart 1070 and a reference signal waveform acquired when the line camera 1010 is installed at the normal installation position. FIG. 20A shows an imaging line 1011 on the installation adjustment chart 1070 captured with the line camera 1010. FIG. 20B shows imaging signals of each of the RGB colors obtained by capturing the image of the installation adjustment chart 1070 on the imaging line 1011 shown in FIG. 20A. The horizontal axis shows the position in the x-axis direction shown in FIG. 20A and the vertical axis shows the brightness value of the imaging signal. In this manner, by obtaining the imaging signal of each of the RGB colors, the abnormality of the light receiving element corresponding to each of the colors of the line camera 1010 can be detected. The brightness value of the imaging signal is low for the black line and high for the white background region between the black lines on the installation adjustment chart 1070.

After adjusting the installation position of the line camera 1010, when the line camera 1010 is installed at the normal installation position at which the printing inspection can be performed, the imaging line 1011 shown in FIG. 20A passes in the rectangular region 1082 having the width L3 shown in FIG. 19A. Because the black lines parallel to the y-axis and the white background continue at a predetermined interval along the entire region in the x-axis direction in this rectangular region 1082, the signal obtained by capturing an image of this rectangular region 1082 has a waveform in which high and low brightness values repeat at a predetermined interval.

FIGS. 21A and 21B are views indicating a relation between the installation adjustment chart 1070 and a signal waveform obtained when the line camera 1010 is rotated about the z-axis shown in FIG. 14 so that the left side thereof is inclined downward. As shown in FIG. 21A, when the line camera 1010 is inclined with respect to a horizontal line, the imaging line 1011 of the line camera 1010 goes out of the rectangular region 1082 having the width L3 shown in FIG. 19A on both the sides across the central line 1071. As a result, only the signals obtained by capturing the patterns 1080b to 1080d and 1081a to 1081c show repeated high and low brightness values, and the signals obtained by capturing the background, by being shifted from the patterns 1080a, 1081d, 1081e, show only high brightness values. As a result, the signal waveforms shown in FIG. 21B are obtained. That is, when the line camera 1010 is inclined with respect to the horizontal line, the obtained signal waveform corresponds to an image in which some of the patterns on the left and some of the patterns on the right of the center of the installation adjustment chart 1070 are not captured. Moreover, the direction of inclination of the line camera 1010 can be recognized from the signal waveform. FIGS. 21A and 21B show an example of a signal waveform in which an image of the leftmost pattern 1081a is captured but the image of the rightmost pattern 1081e is not captured. Accordingly, it can be recognized that the line camera 1010 has been inclined with its left side down.

FIGS. 22A and 22B are views indicating a relation between the installation adjustment chart 1070 and a signal waveform obtained when the line camera 1010 is rotated about the x-axis shown in FIG. 14 so that the front side thereof is down. As shown in FIG. 22A, when the front side of the line camera 1010 is inclined, the imaging line 1011 of the line camera 1010 goes out of the rectangular region having the width L3 shown in FIG. 19A in the entire region. As a result, only the signals obtained by capturing the image of the patterns 1081a to 1081e show repeated high and low brightness values, and the signals obtained by capturing the image of the background, by being shifted from the patterns 1080a to 1080d show only high brightness values. As a result, the signal waveforms shown in FIG. 22B are obtained. That is, when the line camera 1010 is inclined in the front-back direction, the obtained signal waveform corresponds to a signal waveform obtained by capturing all the patterns that are arranged in only the upper part or the lower part of the installation adjustment chart 1070. Moreover, the direction of inclination of the line camera 1010 can be recognized from the signal waveform. FIGS. 22A and 22B show an example of a signal waveform in which an image of the central pattern 1081c is captured. Accordingly, it can be recognized that the line camera 1010 has been inclined with its front side down.

In this manner, the signal waveform obtained by capturing the installation adjustment chart 1070 with the line camera 1010 changes depending on the inclination of the line camera 1010. Accordingly, the line camera 1010 can be installed at the normal installation position by adjusting the inclination of the line camera 1010 while checking the obtained signal waveform so that the reference signal waveform shown in FIG. 20B can be obtained.

The lines at both the ends and the central line 1071 of each of the patterns, and the lines 1073a and 1073b at both the ends of the installation adjustment chart 1070 are thick lines. Therefore, the signal waveform obtained by capturing the installation adjustment chart 1070 has lower brightness values at the positions of these lines than at the other positions. Positions of projecting signals that project downward in the signal waveforms shown in FIGS. 20B, 21B, and 22B correspond to the positions of these thick lines. In the signal waveform obtained by capturing the installation adjustment chart 1070, the interval between the projecting signals is narrow only in the center part. Therefore, the correspondence between the installation adjustment chart 1070 and the signal waveform can be recognized from the positions at which the projecting signals appear.

Figure 23A:
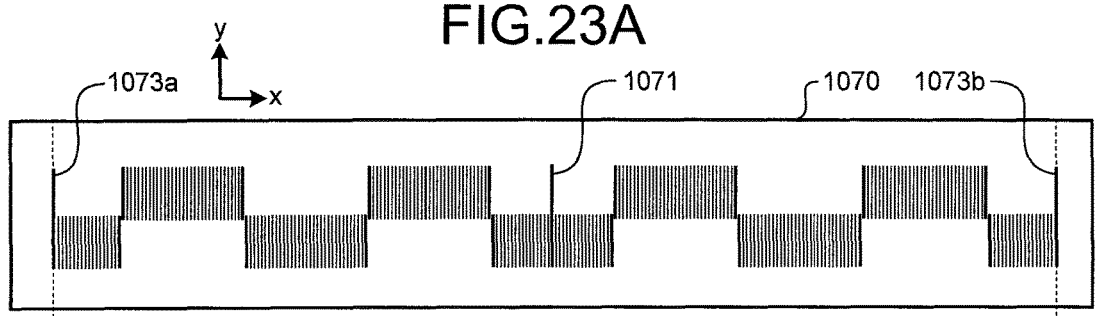
FIGS. 23A to 23C are views of exemplary installation adjustment charts observed at various installation positions of the line camera.
Figure 23B:
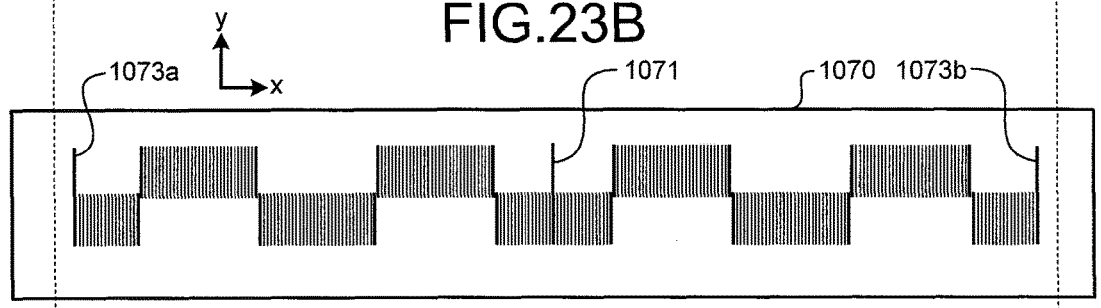
Figure 23C:
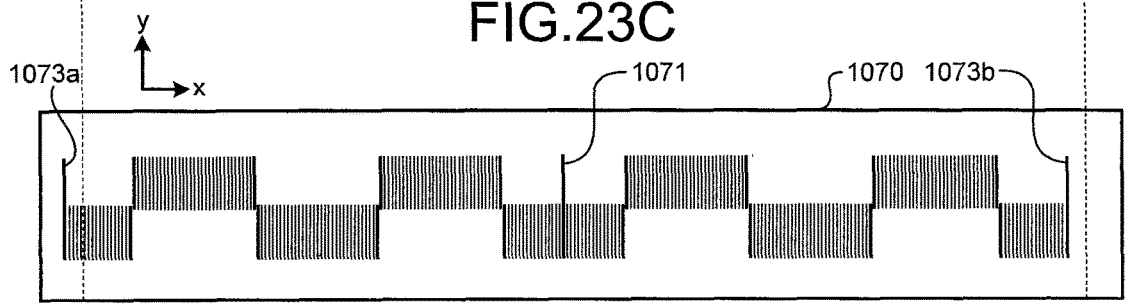

Subsequently, the installation adjustment of the line camera 1010 performed based on the projecting signals in the signal waveform obtained by capturing the installation adjustment chart 1070 is explained. FIGS. 23A to 23C are views of the exemplary installation adjustment charts 1070 observed from various installation positions of the line camera 1010. FIG. 23A shows the installation adjustment chart 1070 observed when the line camera 1010 is installed at the normal installation position.

FIG. 23B shows the installation adjustment chart 1070 observed when the line camera 1010 is installed at a position that is away from the inspection drum 1020 than the normal installation position. Because the distance from the installation adjustment chart 1070 to the line camera 1010 is longer than when the line camera 1010 is installed at the normal installation position, the distance between the lines 1073a and 1073b at both the ends in FIG. 23B is shorter than the distance between the lines 1073a and 1073b at both the ends in FIG. 23A. That is, the installation adjustment chart 1070 appears to be reduced in size when observed from an installation position that is farther away from the normal installation position. Conversely, the installation adjustment chart 1070 appears to be enlarged in size when observed from the installation position that is nearer than the normal installation position.

FIG. 23C shows the installation adjustment chart 1070 observed when the line camera 1010 is installed at the normal installation position but with the front side thereof rotated about the y-axis toward the right direction. Because the line camera 1010 has been installed such that it faces toward the right than when installed at the normal installation position, in FIG. 23C, the entire installation adjustment chart 1070, including the central line 1071 and the lines 1073a and 1073b at both the ends, is observed to be shifted in the left direction in comparison with FIG. 23A. Conversely, when the line camera 1010 is installed at the normal installation position but rotated about the y-axis toward the left direction, the entire installation adjustment chart 1070 will be observed to be shifted toward the right direction.

Figure 24A:
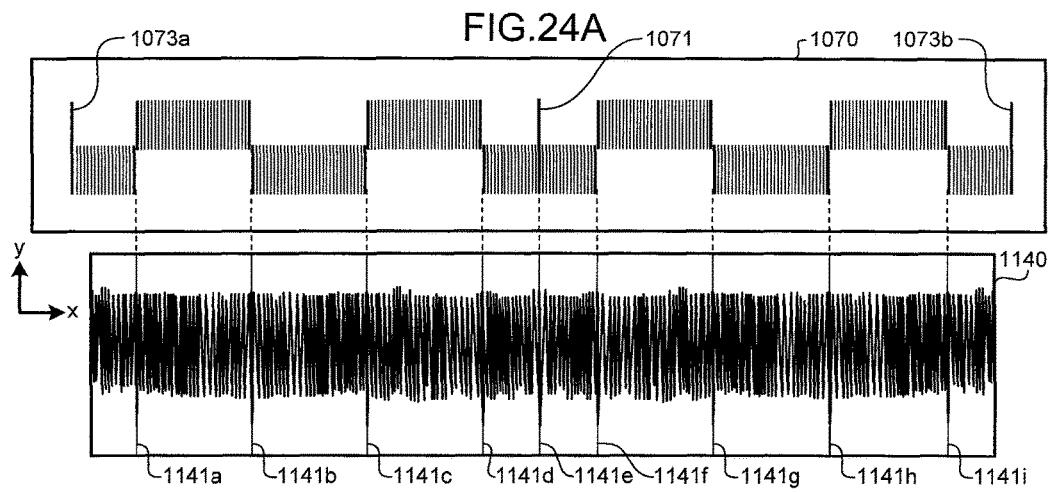
FIGS. 24A to 24C are views indicating a relation between the installation adjustment charts shown in FIGS. 23A to 23C and the signal waveforms of imaging signals observed at each installation positions of the line camera.
Figure 24B:
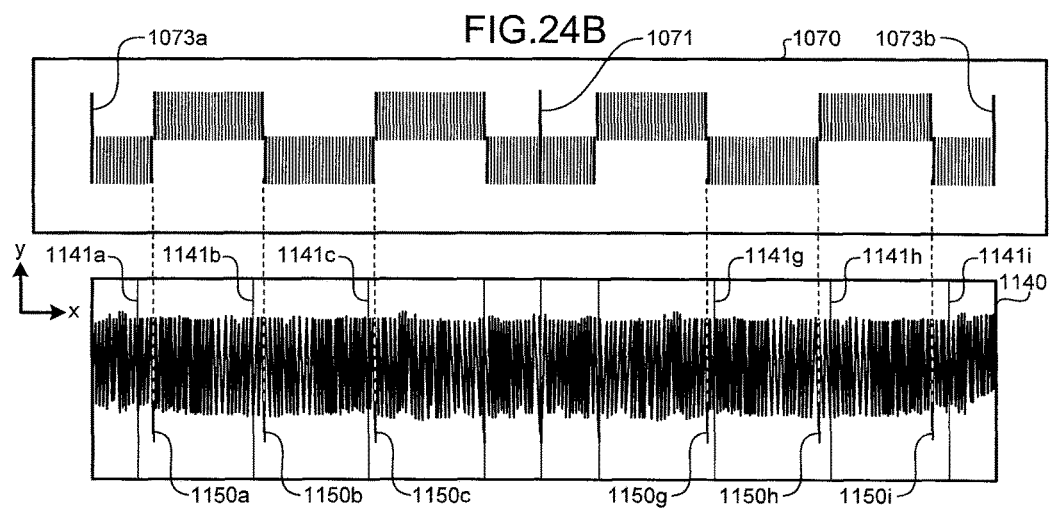
Figure 24C:
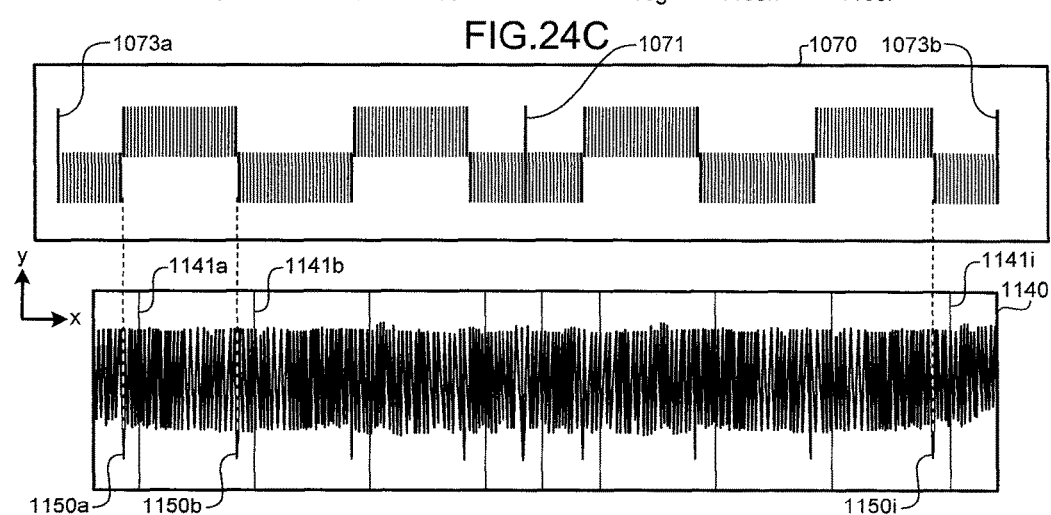

FIGS. 24A to 24C are views indicating a relation between the installation adjustment charts 1070 shown in FIGS. 23A to 23C and the signal waveforms of the imaging signal observed at each installation positions of the line camera 1010. In FIGS. 24A to 24C, in the upper part is shown the installation adjustment chart 1070 observed in each of the positions shown in FIGS. 23A to 23C, and in the lower part is shown a screen 1140 of the display unit 1050 on which is displayed the signal waveform obtained by capturing the corresponding installation adjustment chart 1070 with the line camera 1010. On the screen 1140 shown in FIGS. 24A to 24C, the horizontal axis shows the position of the installation adjustment chart 1070 in the x-axis direction, and the vertical axis shows the brightness value of the imaging signal. FIGS. 24A to 24C show the signal waveforms of the imaging signal in a state in which the line camera 1010 is not rotated about the x-axis and the z-axis.

In the reference signal waveform obtained by capturing the installation adjustment chart 1070 with the line camera 1010 installed at the normal installation position, a projecting signal that projects in the downward direction appears at the positions of the lines at both the ends of each of the patterns that are shifted vertically, the central line 1071, and the lines 1073a and 1073b at both the ends of the installation adjustment chart 1070. As shown in FIG. 24A, reference lines 1141a to 1141i indicating the positions of these projecting signals are displayed on the screen 1140 of the display unit 1050. In this manner, a signal waveform in which high and low brightness values are repeated is displayed over the entire screen 1140 and, when the positions of the projecting signals of this signal waveform correspond with the positions of the reference lines 1141*a* to 1141*i*, it means that the line camera 1010 is installed at the normal installation position. That is, the line camera 1010 can be installed at the normal installation position by adjusting the position of the line camera 1010 such that the signal waveform obtained by capturing the installation adjustment chart 1070 with the line camera 1010 and displayed on the screen 1140 of the display unit 1050 matches with the reference signal waveform shown in FIG. 24A.

When, as shown in FIG. 24B, the line camera 1010 is installed at a position that is away from the inspection drum 1020 than the normal installation position, in the signal waveform obtained by capturing the installation adjustment chart 1070, projecting signals 1150*a* to 1150*c* located on the left of the center appear at positions that are shifted to the right side of the reference lines 1141*a* to 1141*c* on the screen 1140. Moreover, projecting signals 1150*g* to 1150*i* located on the right of the center appear at positions that are shifted to the left side of the reference lines 1141*g* to 1141*i*. In this manner, when a signal waveform appears on the screen 1140 of the display unit 1050 in which the projecting signals at both the outer sides are shifted toward the center from the corresponding reference lines, it can be recognized that the line camera 1010 is installed at a position that is away from the inspection drum 1020 than the normal installation position. Conversely, when a signal waveform appears in which the projecting signals 1150*a* to 1150*c* and 1150*g* to 1150*i* at both the outer sides are shifted toward the outer side from the corresponding reference lines 1141*a* to 1141*c* and 1141*g* to 1141*i*, it can be recognized that the line camera 1010 is installed at a position that is nearer to the inspection drum 1020 than the normal installation position.

When the line camera 1010 is installed at the normal installation position but with the front side thereof rotated about the y-axis toward the right direction, as shown in FIG. 24C, in the signal waveform obtained by capturing the installation adjustment chart 1070, all the projecting signals 1150*a* to 1150*i* appear at the positions that are shifted toward the left of the reference lines 1141*a* to 1141*i*. When such a signal waveform is obtained, it can be recognized that the line camera 1010 has been installed at the normal installation position but with the front side thereof rotated about the y-axis toward the right direction. Conversely, when a signal waveform appears in which all the projecting signals 1150*a* to 1150*i* are shifted toward the right of the corresponding reference lines 1141*a* to 1141*i*, it can be recognized that the line camera 1010 has been installed at the normal installation position but with the front side thereof rotated about the y-axis toward the left direction.

The installation status of the line camera 1010 can be recognized from the positions of the projecting signals appearing in the signal waveform obtained by capturing the installation adjustment chart 1070 with the line camera 1010 and the positions of the reference lines 1141*a* to 1141*i* displayed on the screen 1140 of the display unit 1050. Therefore, the line camera 1010 can be installed at the normal installation position by, depending on the current installation status, correcting the installation position of the line camera 1010 so that the positions of the projecting signals match with the corresponding reference lines on the screen 1140.

A method for correcting the installation position of the line camera 1010 is explained by using FIGS. 19A to 19C. When the line camera 1010 is installed at the normal installation position, the width (L2 shown in FIG. 19C) in the x-axis direction of the patterns 1080*a* and 1080*d* shown in FIG. 19A and the width of the signal waveform corresponding to this width have a predetermined value. The installation position of the line camera 1010 is corrected by using this fact. Specifically, the width of the signal waveform corresponding to the width of the patterns 1080*a* and 1080*d* in the x-axis direction is shorter than the predetermined value when the distance from the line camera 1010 to the inspection drum 1020 is longer than when the line camera 1010 is installed at the normal setting position. Therefore, it can be understood that the line camera 1010 needs to be moved closer to the inspection drum 1020 to match the position of the line camera 1010 to the normal installation position. Conversely, the width of the signal waveform corresponding to the width of the patterns 1080*a* and 1080*d* in the x-axis direction will be longer than the predetermined value when the distance from the line camera 1010 to the inspection drum 1020 is shorter. Therefore, it can be understood that the line camera 1010 needs to be moved away from the inspection drum 1020 to match the position of the line camera 1010 to the normal installation position. Furthermore, when the line camera 1010 is inclined with respect to the inspection drum 1020, the width of the signal waveform obtained from the pattern 1080*d* is different from the width of the signal waveform obtained from the pattern 1080*a*. For example, when the width of the signal waveform indicating the pattern 1080*a* is shorter than the width of the signal waveform indicating the pattern 1080*d*, the line camera 1010 has been installed in a state in which the pattern having the shorter width is positioned away from the inspection drum 1020 than the pattern having the longer width. Accordingly, the installation position of the line camera 1010 needs to be corrected to address this issue.

The camera-position judging unit 1062 shown in FIG. 15 judges the installation status of the line camera 1010 based on the signal waveform obtained from the line camera 1010 that captures the installation adjustment chart 1070, and outputs information about the installation status and a correction policy. The outputting of the information is performed by displaying on the display unit 1050 of information about an installation adjustment, playing of a predetermined alarm sound, playing of a predetermined voice, and the like.

For example, when the signal waveform shown in FIG. 21B is obtained, the camera-position judging unit 1062 recognizes that the line camera 1010 has been inclined downward at the left side. In this case, the camera-position judging unit 1062 outputs information that indicates that the line camera 1010 is inclined downward at the left side, and information that prompts the user to correct the inclination by rotating the line camera 1010 toward the right direction. Moreover, when the signal waveform shown in FIG. 22B is obtained, the camera-position judging unit 1062 recognizes that the front part of the line camera 1010 has been inclined down. In this case, the camera-position judging unit 1062 outputs information that indicates this fact, and information that prompts the user to correct the inclination by rotating the line camera 1010 so that its front part goes up.

Likewise, when the signal waveform shown in FIG. 24B is obtained, the camera-position judging unit 1062 recognizes that the line camera 1010 is installed in the back at a position that is away from the inspection drum 1020 than the normal installation position. In this case, the camera-position judging unit 1062 outputs information that indicates this fact, and information that prompts the user to move the line camera 1010 forward. Moreover, when the signal waveform shown in FIG. 24C is obtained, the camera-position judging unit 1062 recognizes that the line camera 1010 has been installed at the normal installation position but rotated about the y-axis toward the right direction. In this case, the camera-position judging unit 1062 outputs information that indicates this fact, and information that prompts the user to rotate the line camera 1010 about the y-axis toward the left direction.

When the user operates the adjustment mechanism of the camera holder of the line camera 1010 based on the information output by the camera-position judging unit 1062, the installation position of the line camera 1010 is gradually changed. When the installation position of the line camera 1010 coincides with the normal installation position, the reference signal waveforms shown in FIGS. 20B and 24A will be obtained. Upon recognizing that the installation position of the line camera 1010 has been corrected to the normal installation position because the reference signal waveforms shown in FIGS. 20B and 24A have been obtained, the camera-position judging unit 1062 outputs information to indicate this fact. After checking this information, the user stops the operation of the adjustment mechanism of the camera holder. In this manner, the line camera 1010 can be installed at the normal installation position. Moreover, when the operation to adjust the installation position of the line camera 1010 is being performed in the wrong direction whereby the position misalignment or the inclination of the installation position is increasing, the camera-position judging unit 1062 outputs information to indicate that the adjustment direction is wrong. After checking this information, the user can correct the adjustment direction. The camera-position judging unit 1062 stores the reference signal waveform obtained when the line camera 1010 is installed at the normal installation position, displays on the display unit 1050 the reference signal waveform and the signal waveform of the line camera 1010 whose position is being adjusted allowing comparison thereof, and performs a judgment relating to the installation adjustment.

The installation adjustment chart 1070 according to the present embodiment is not limited to those shown in FIGS. 19A to 19C. For example, with respect to the design of the rectangular region 1082 having the width L3 shown in FIG. 19A, as long as it is possible to recognize that the imaging line of the line camera 1010 is in the rectangular region 1082, it is not limited that the rectangular region 1082 has a pattern in which the white background and the black lines continue at a predetermined interval. For example, it is allowable that only a partial region in the rectangular region 1082 has a white background and black lines. Moreover, with respect to the shape of the patterns 1080a to 1080d and 1081a to 1081e that are arranged by shifting alternately in the vertical direction, for example, as shown in FIG. 21A, as long as it is possible to recognize that the imaging line 1011 is out of the rectangular region 1082 having the width L3 due to the inclination or the position misalignment of the line camera 1010, it is not limited that these patterns have a rectangular shape. That is, these patterns can have a concave shape, a convex shape, and the like. Likewise, with respect to the arrangement of the patterns 1080a to 1080d and 1081a to 1081e, as long as it is possible to recognize that the imaging line 1011 is out of the rectangular region 1082 having the width L3 due to the inclination or the position misalignment of the line camera 1010, it is not limited to arrange these patterns by shifting alternately in the vertical direction. For example, it is allowable to generate the installation adjustment chart 1070 with only the pattern 1081c, which includes the central line 1071 shown in FIGS. 19A and 19B, and some of the patterns on both the outer sides. Moreover, with respect to the thickness and the arrangement of each of the lines, for example, as shown in FIGS. 24B and 24C, as long as it is possible to recognize the inclination and the position misalignment of the line camera 1010 from the signal waveform, a thick line can be drawn at a predetermined position other than at which they have been drawn in the present embodiment. It is not limited that the lines are drawn at a regular interval. For example, the lines can be drawn at non-regular intervals but with certain regularity.

As explained earlier, according to the present embodiment, the installation adjustment chart 1070 including the predetermined patterns that allow the detection of the inclination and the position misalignment of the line camera 1010 is captured with the line camera 1010, the inclination and the position misalignment of the line camera 1010 are recognized based on the obtained signal waveform, and the installation position of the line camera 1010 is corrected.

Moreover, because the directions of the inclination and the position misalignment of the line camera 1010 can be recognized from the signal waveform obtained by capturing the installation adjustment chart 1070 with the line camera 1010, the contents of the installation adjustment operation that needs to be performed to correct the inclination and the position misalignment of the line camera 1010 can be recognized.

Moreover, the information is output that indicates that the inclination and the position misalignment of the line camera 1010 are recognized, the direction of correction of the inclination and the position misalignment, the fact that the inclination and the position misalignment have been corrected and the line camera 1010 has been installed at the normal installation position, the fact that the adjustment direction of the installation position is wrong, and the like. Accordingly, based on the output information, the installation adjustment operation for correcting the inclination and the position misalignment of the line camera 1010 can be performed easily.

INDUSTRIAL APPLICABILITY

As explained above, the method and the apparatus for removing character background from the color image according to the present invention are useful in acquiring a character image by removing a background design of the character from a color image obtained by capturing a color printed object containing the character, and evaluating the printing quality of the character. Moreover, the method and the installation adjustment chart of a line camera according to the present invention are useful in allowing an installation position of the line camera that captures an image of a large-size printed object to be adjusted easily.

EXPLANATION OF REFERENCE NUMERALS

10, 1010 Line camera
20, 1020 Inspection drum
30, 1030 Light source
40, 1040 Inspection-drum driving unit
50 Operation/display unit
60 Memory
70, 1060 Control unit
71 Color-image acquiring unit 72, 1063 Light-source control unit
74 Character recognition unit
75 Character-background removing unit
76, 1065 Printing inspection unit
200, 1200 Large-size printed object
1050 Display unit
1061 Camera-signal processing unit
1062 Camera-position judging unit
1070 Chart for installation adjustment

The invention claimed is:

1. A method for removing character background from a color image in order to obtain an image for printing evaluation by removing a background design of a character from a color image of a printed object on which the character has been printed, comprising:
   capturing the color image of the printed object;
   cutting out an image of a partial region including the character from the color image of the printed object as an input image;
   separating the input image into a character part and a background part by identifying a position at which a font image of the character contained in the input image overlaps with the character contained in the input image, and determining, among pixels that form the input image, pixels at a position overlapping the font image as a character part and pixels at a position not overlapping the font image as a background part;
   calculating a discriminant function for separating pixels of the character part and pixels of the background part based on pixel values; and
   generating a background-removed image by removing the background part from the input image by using the discriminant function.

2. The method for removing character background from a color image as claimed in claim 1, wherein the calculating includes calculating the discriminant function by performing linear distinction processing.

3. The method for removing character background from a color image as claimed in claim 1, further comprising specifying a character range for calculating the discriminant function, wherein
   the separating includes separating the input image into the character part and the background part based on the character range specified at the specifying, and
   the calculating includes calculating the discriminant function based on the character range specified at the specifying.

4. The method for removing character background from a color image as claimed in claim 1, wherein the method is performed for every character when a plurality of characters is contained in the input image.

5. The method for removing character background from a color image as claimed in claim 1, further comprising performing binarization of the background-removed image to remove the background design having a similar color as a color of the character.

6. The method for removing character background from a color image as claimed in claim 1, wherein the printed object is a large-size printed object.

7. A character background removing apparatus that obtains an image for printing evaluation by removing a background design of a character from a color image of a printed object on which the character has been printed, comprising:
   a color image acquiring unit that captures the color image of the printed object and cuts out an image of a partial region including the character from the color image of the printed object as an input image; and
   a character-background removing unit that separates the input image into a character part and a background part by identifying a position at which a font image of the character contained in the input image overlaps with the character contained in the input image, and determining, among pixels that form the input image, pixels at a position overlapping the font image as a character part and pixels at a position not overlapping the font image as a background part;
   calculates a discriminant function for separating pixels of the character part and pixels of the background part based on pixel values, and
   generates a background-removed image by removing the background part from the input image by using the discriminant function.

8. A character background removing apparatus that obtains an image for printing evaluation by removing a background design of a character from a color image of a printed object on which the character has been printed, comprising:
   a color image acquiring unit that captures the color image of the printed object and cuts out an image of a partial region including the character from the color image of the printed object as an input image;
   an operation unit that specifies a position of the character on the input image; and
   a character-background removing unit that
      separates the input image into a character part and a background part based on the position of the character specified by the operation unit,
      calculates a discriminant function for separating pixels of the character part and pixels of the background part based on pixel values, and
      generates a background-removed image by removing a background design by using the discriminant function.

* * * * *